United States Patent [19]

Buchanan

[11] Patent Number: 5,752,825
[45] Date of Patent: May 19, 1998

[54] ENDODONTIC TREATMENT SYSTEM

[76] Inventor: Leonard Stephen Buchanan, 2335 Foothill La., Santa Barbara, Calif. 93105

[21] Appl. No.: 653,323

[22] Filed: May 24, 1996

Related U.S. Application Data

[62] Division of Ser. No. 234,290, Apr. 28, 1994.

[51] Int. Cl.$^6$ .................... A61C 3/00; A61C 19/00
[52] U.S. Cl. .................................. 433/32; 433/102
[58] Field of Search ................. 433/32, 81, 102, 433/224

[56] References Cited

U.S. PATENT DOCUMENTS

| | | |
|---|---|---|
| D. 250,544 | 12/1978 | Leonard . |
| 251,598 | 12/1881 | Johanson . |
| D. 283,840 | 5/1986 | Matsutani . |
| 375,427 | 12/1887 | Richards ........................ 433/81 |
| 1,307,446 | 6/1919 | Kerr . |
| 1,684,143 | 9/1928 | Pieper et al. .................. 433/32 X |
| 1,792,120 | 2/1931 | Pieper ........................... 433/32 |
| 2,418,214 | 4/1947 | Yeager et al. ................. 433/32 |
| 3,330,040 | 7/1967 | Kahn . |
| 3,908,270 | 9/1975 | Fishman . |
| 4,231,738 | 11/1980 | Riitano et al. . |
| 4,280,808 | 7/1981 | Johnson et al. . |
| 4,299,571 | 11/1981 | McSpadden . |
| 4,332,561 | 6/1982 | McSpadden . |
| 4,340,364 | 7/1982 | Deemer . |
| 4,443,193 | 4/1984 | Roane . |
| 4,518,356 | 5/1985 | Green . |
| 4,527,560 | 7/1985 | Masreliez . |
| 4,536,159 | 8/1985 | Roane . |
| 4,538,989 | 9/1985 | Apairo, Jr. et al. . |
| 4,634,378 | 1/1987 | Leonard . |
| 4,674,979 | 6/1987 | Jacklich . |
| 4,836,780 | 6/1989 | Buchanan . |
| 4,850,867 | 7/1989 | Senia et al. . |
| 4,934,934 | 6/1990 | Arpaio, Jr. et al. . |
| 4,971,556 | 11/1990 | Ritano ........................... 433/102 |
| 5,017,138 | 5/1991 | Schilder . |
| 5,026,284 | 6/1991 | Martin . |
| 5,125,838 | 6/1992 | Seigneurin . |
| 5,219,284 | 6/1993 | Velvart et al. ................. 433/102 |

FOREIGN PATENT DOCUMENTS

| | | |
|---|---|---|
| A-0 257 961 | 8/1987 | European Pat. Off. . |
| A-0 501 255 | 2/1992 | European Pat. Off. . |
| A-2 597 327 | 4/1986 | France . |
| A-2 617 704 | 7/1988 | France . |
| A-2 647 663 | 6/1989 | France . |
| A-291 668 | 6/1951 | Switzerland . |
| A-657 981 | 4/1984 | Switzerland . |

OTHER PUBLICATIONS

MANI Apical Reamer, Matsutani Seisakusho Co., Ltd. (four pages).

Single–Step Engine Reamer, Dental Products Report Jun., 1988 (one page).

*Primary Examiner*—Nicholas D. Lucchesi
*Attorney, Agent, or Firm*—Henry M. Bissell

[57] ABSTRACT

An endodontic system of shaping instruments, irrigation cannulas, filling instruments and materials designed to safely create specific tapers of root canal preparations and to clean, dry, seal, and restore them. The shaping instruments are a series of reamers, files, and handpiece burs, made of stainless steel, nickel-titanium, or other alloys, which impart several different specifically-tapered apertures in root canals. The instruments have one or more safety features to eliminate perforating curved roots, including shorter flute length as the angle of taper increases and variable sharpness along the length of the flute portion, as well as variable flute pitch along the length of the flute portion to maximize cutting efficiency and resistance to breakage, and a rounded tip to eliminate ledging. The hand instruments have a handle designed to optimize use of the instruments in apically directed, rotary cutting motions. The irrigation cannulas, the condensation heat carriers, pluggers, injection needles, and backfillers, and the materials, including drying paper points, filling materials, and restorative post systems, have shapes which match the canal tapers created by the shaping instruments.

13 Claims, 14 Drawing Sheets

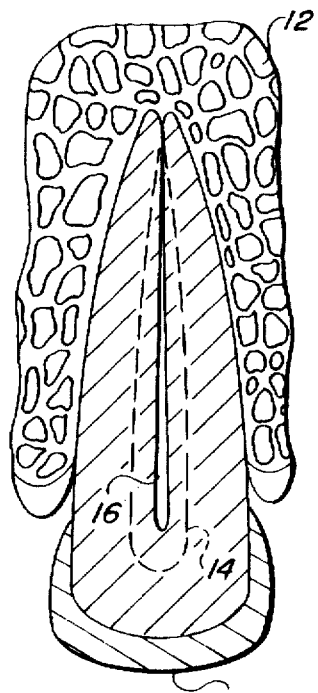
FIG-1
(PRIOR ART)
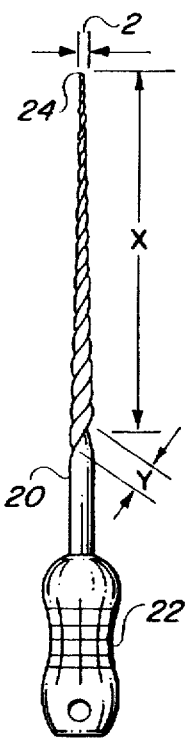
FIG-1A
(PRIOR ART)
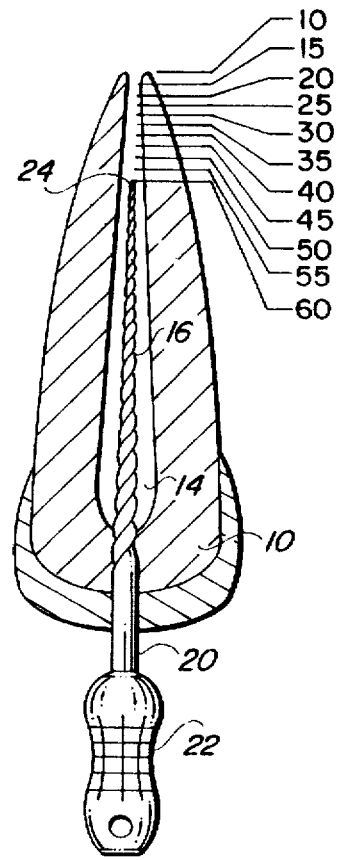
FIG-2
(PRIOR ART)
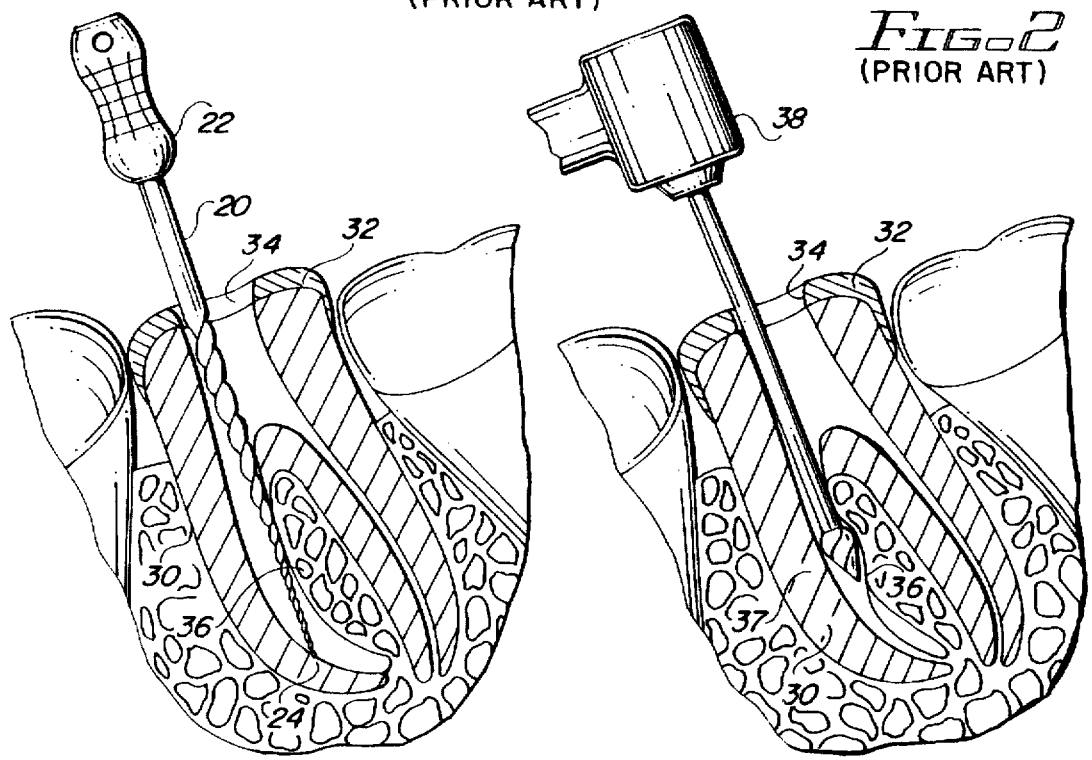
FIG-3
(PRIOR ART)
FIG-3A
(PRIOR ART)

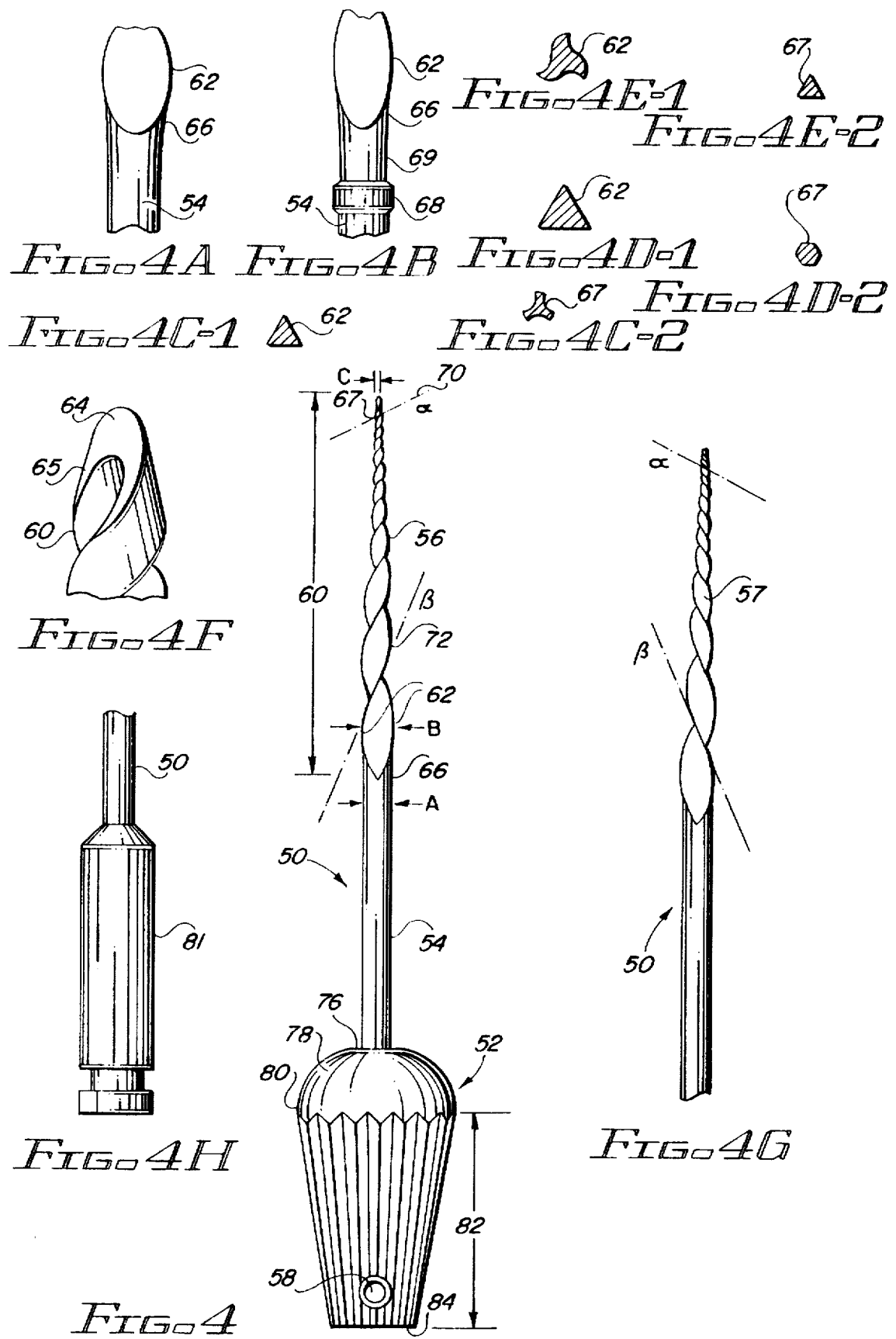

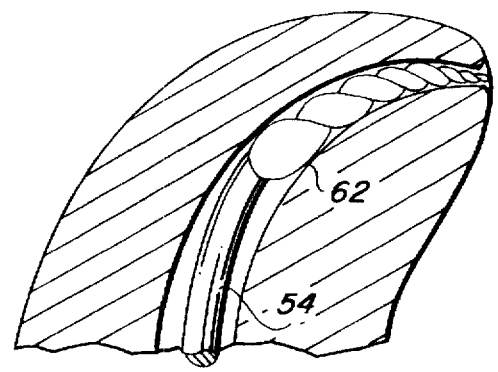
FIG.-6A
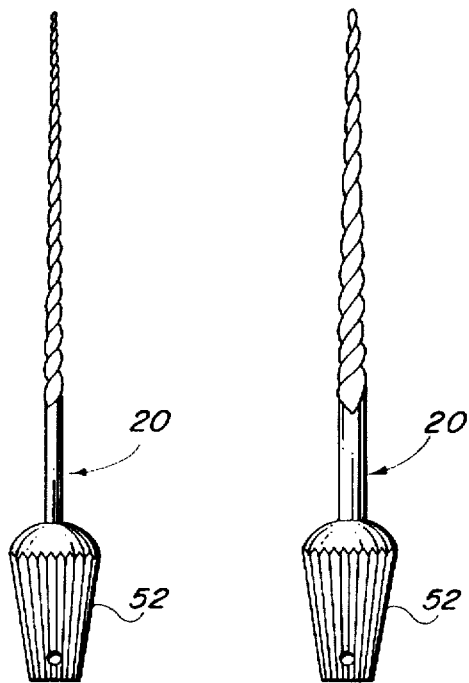
FIG.-5A  FIG.-5B
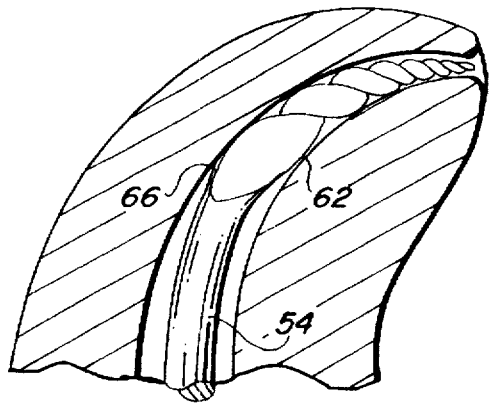
FIG.-6B
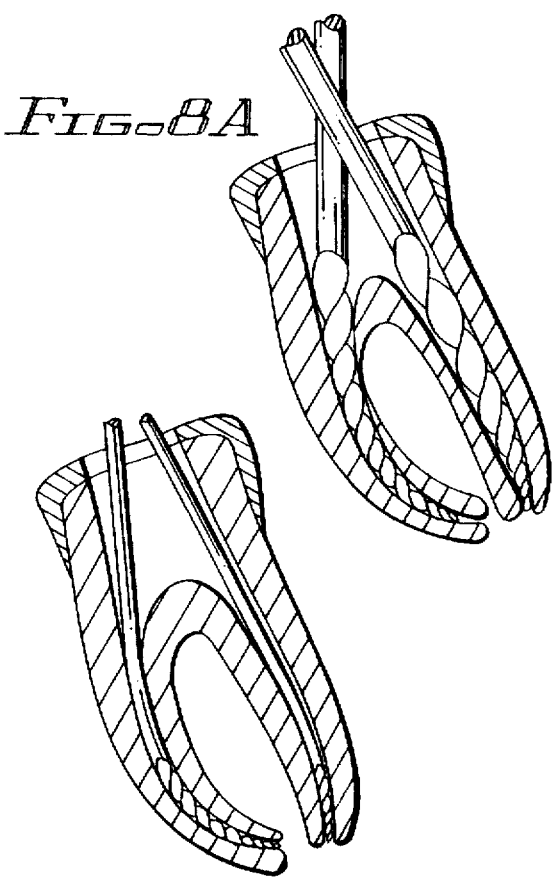
FIG.-8A
FIG.-8B
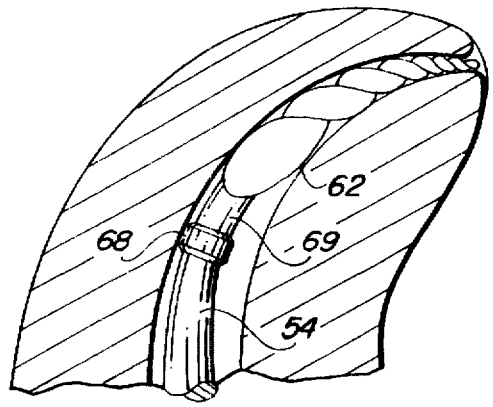
FIG.-6C

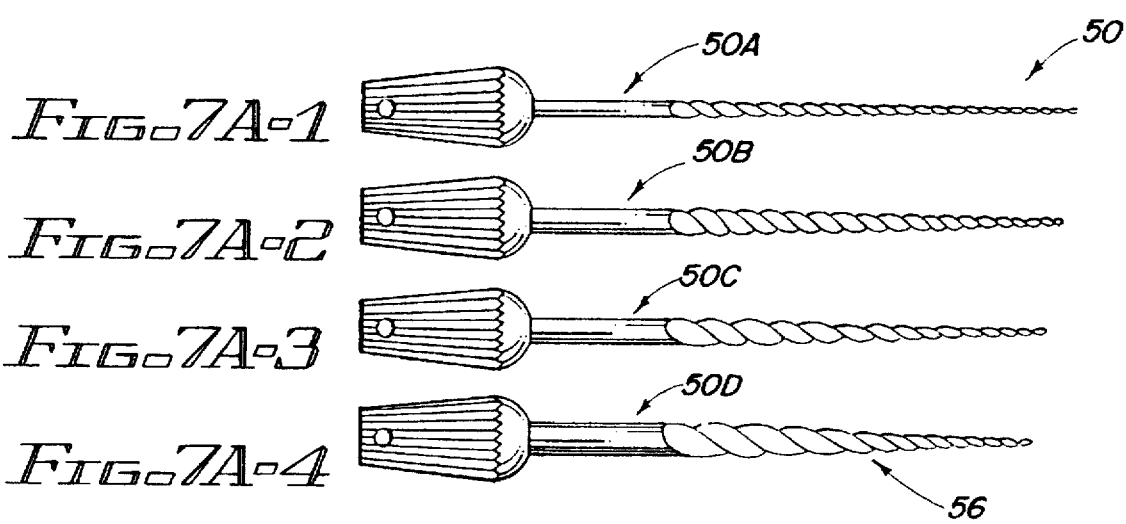
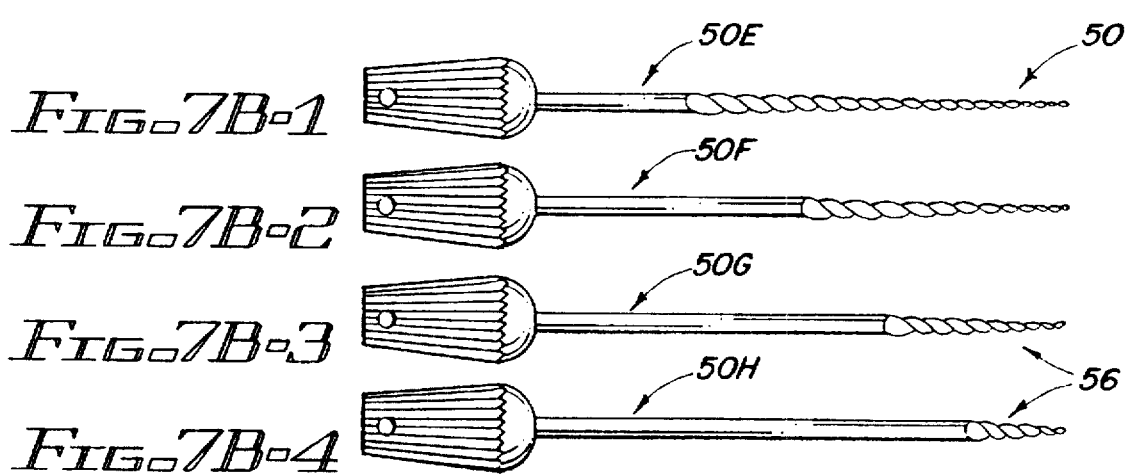
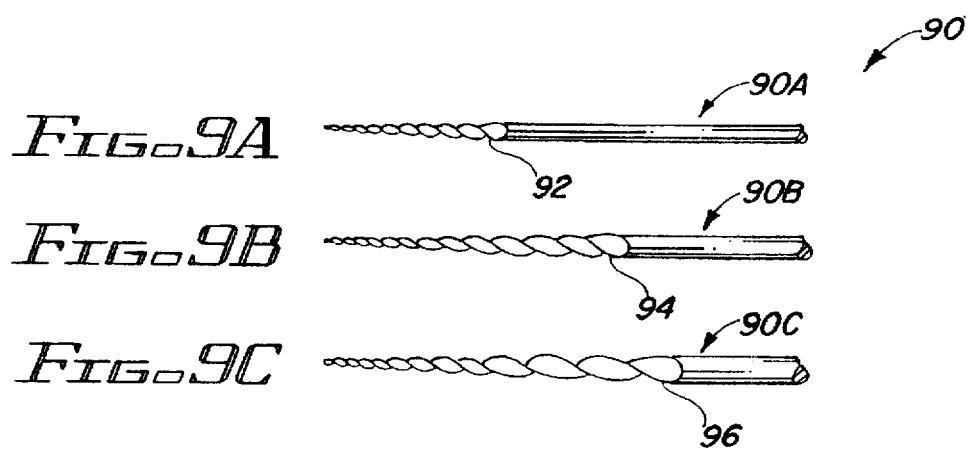

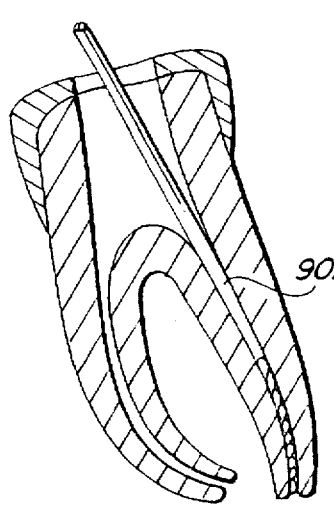 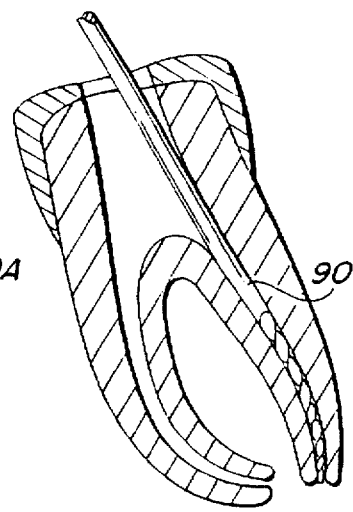 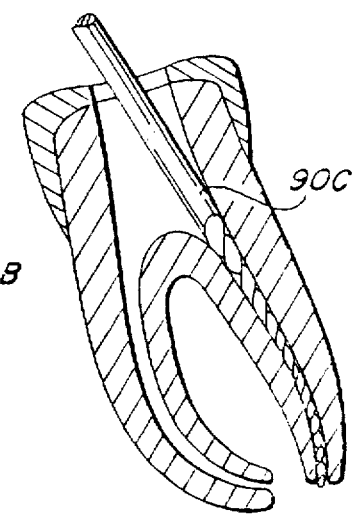
FIG.11A     FIG.11B     FIG.11C
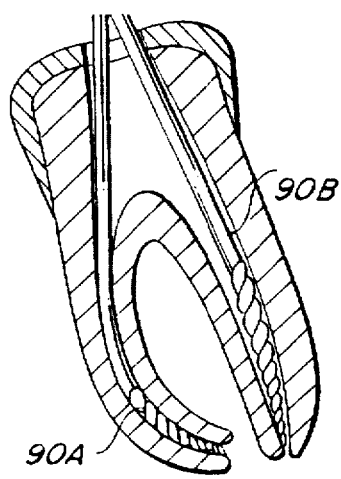 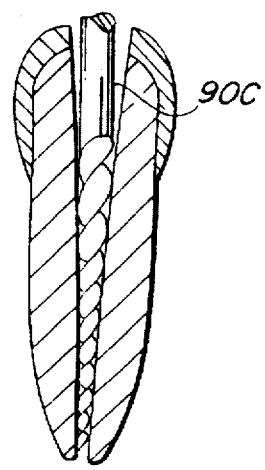
FIG.10A     FIG.10B
FIG.15E-1     FIG.15E-2     FIG.15E-3

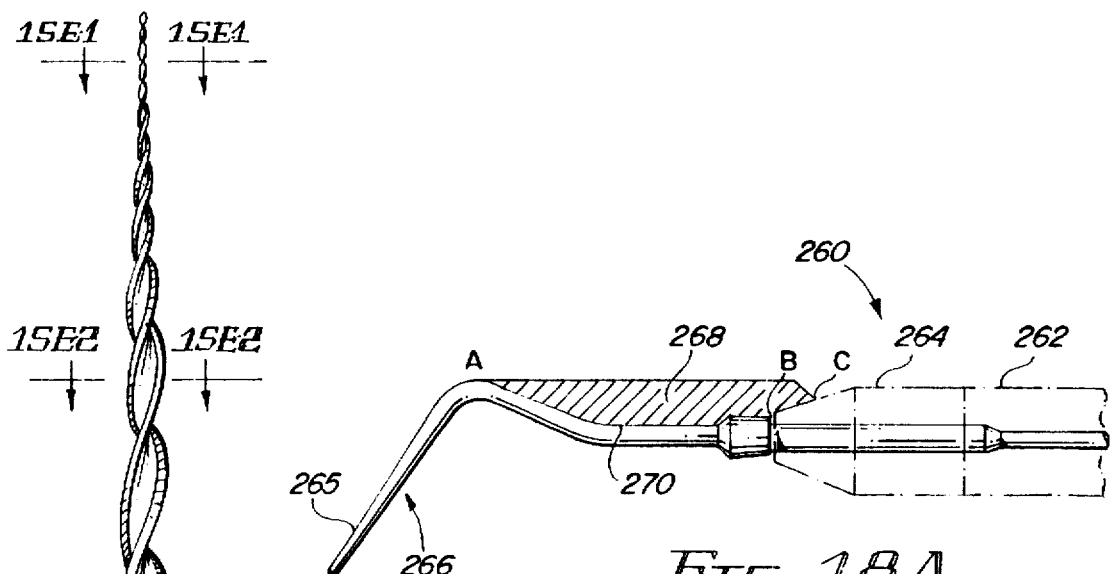
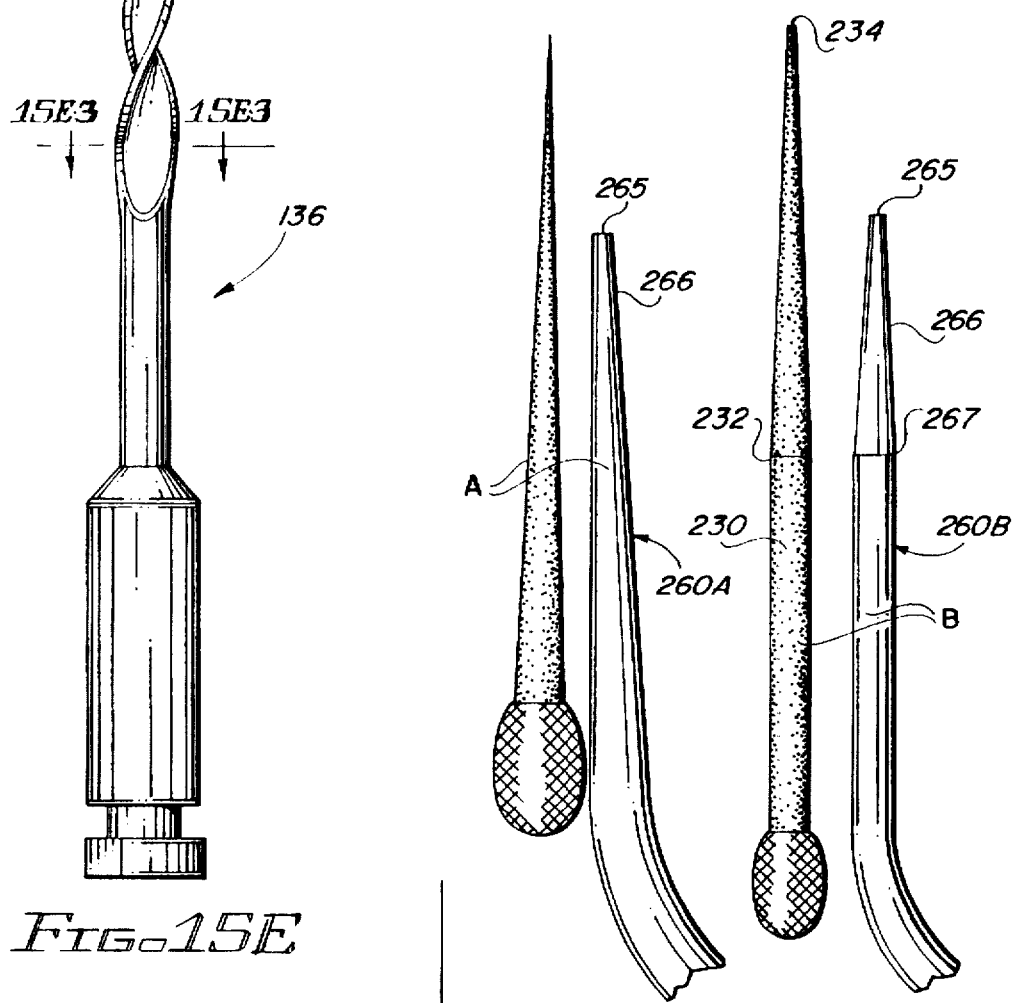
FIG.15E
FIG.18A
FIG.18B

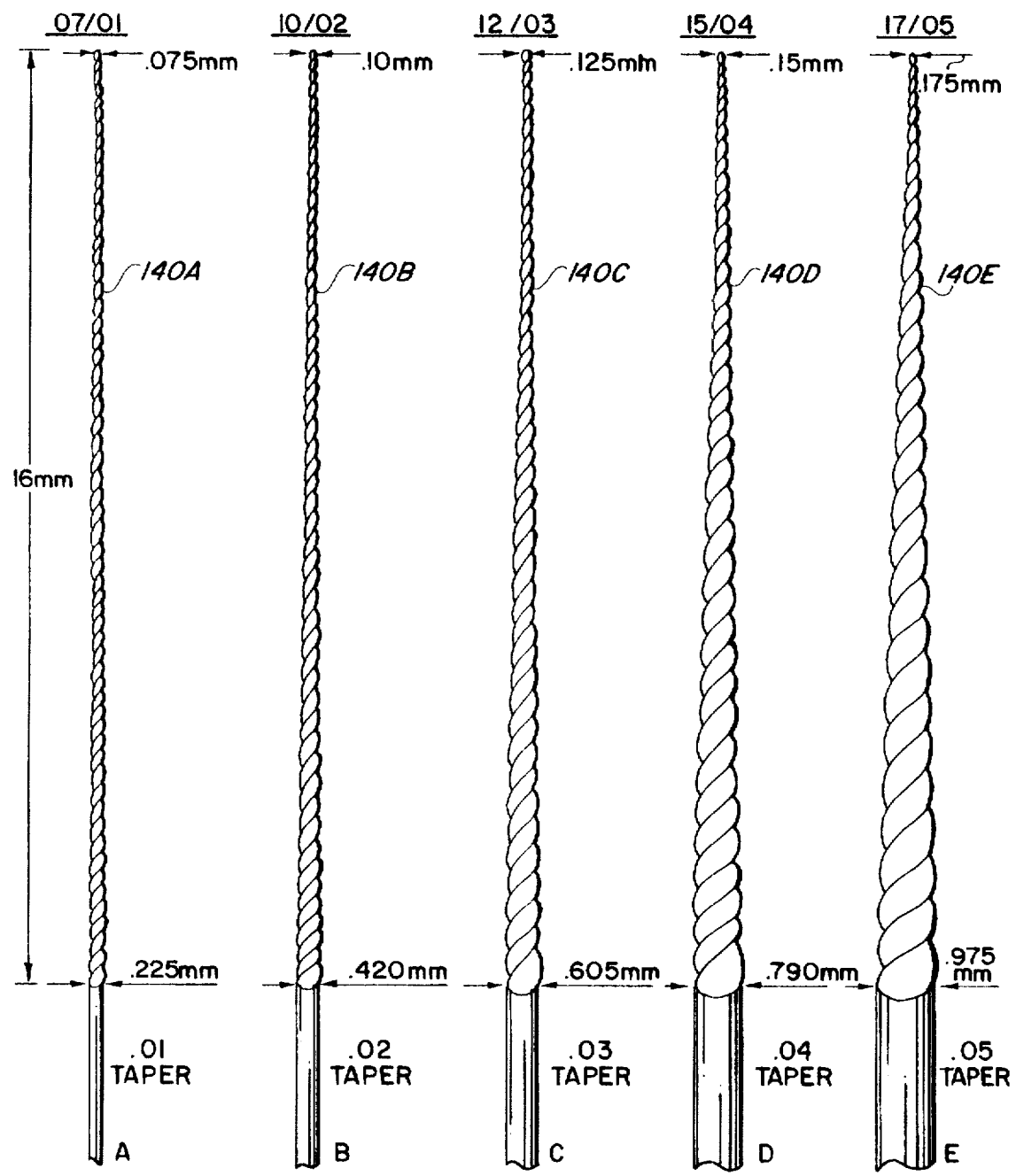

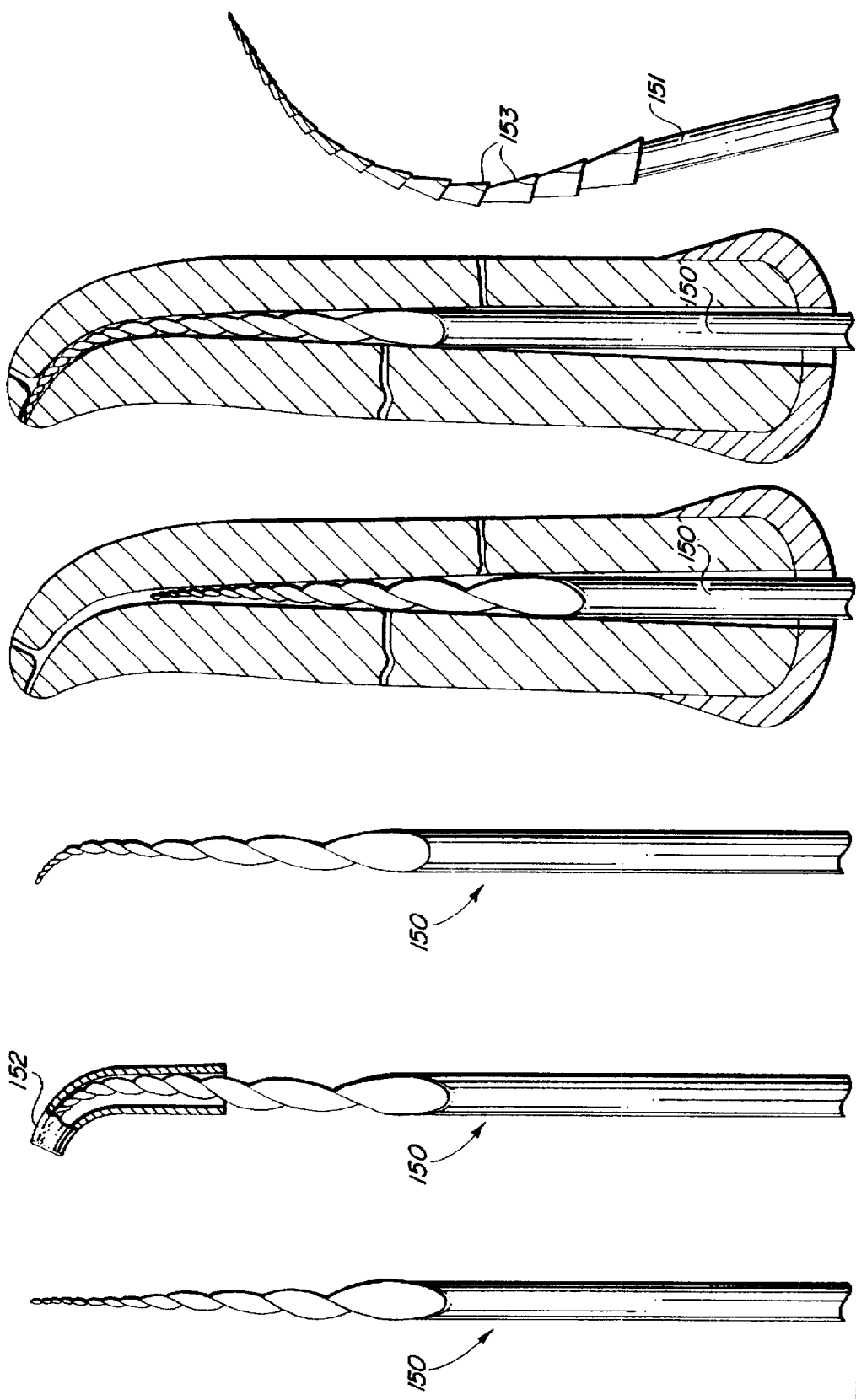

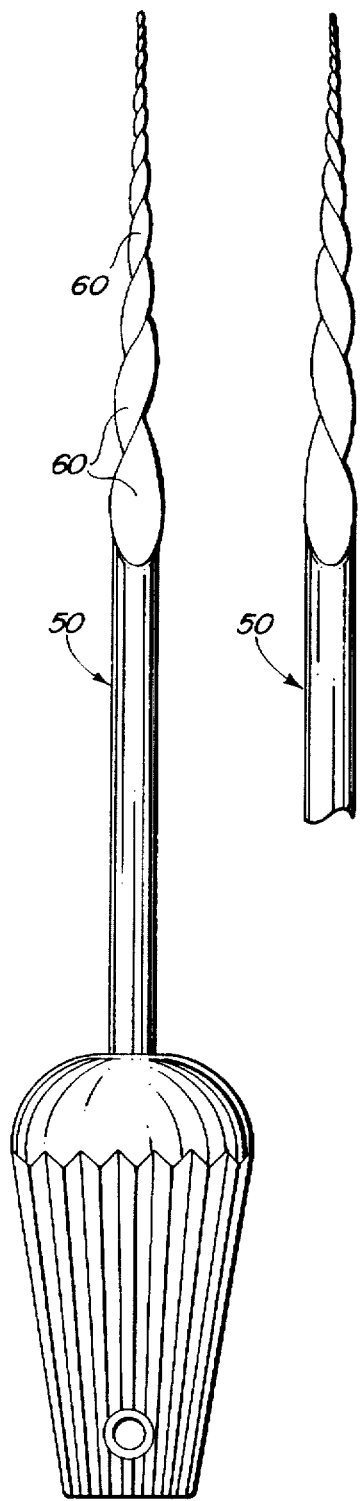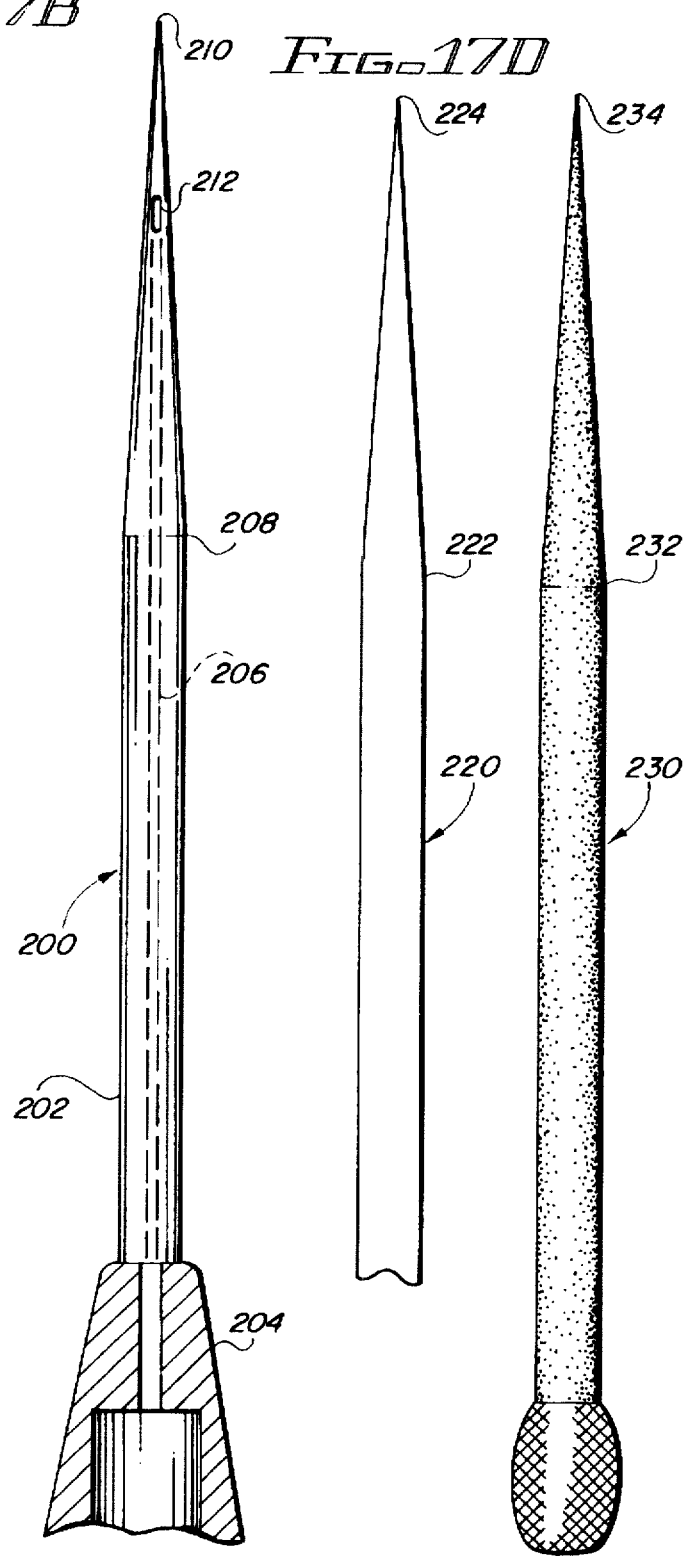
FIG. 17A  FIG. 17B  FIG. 17C  FIG. 17D  FIG. 17E

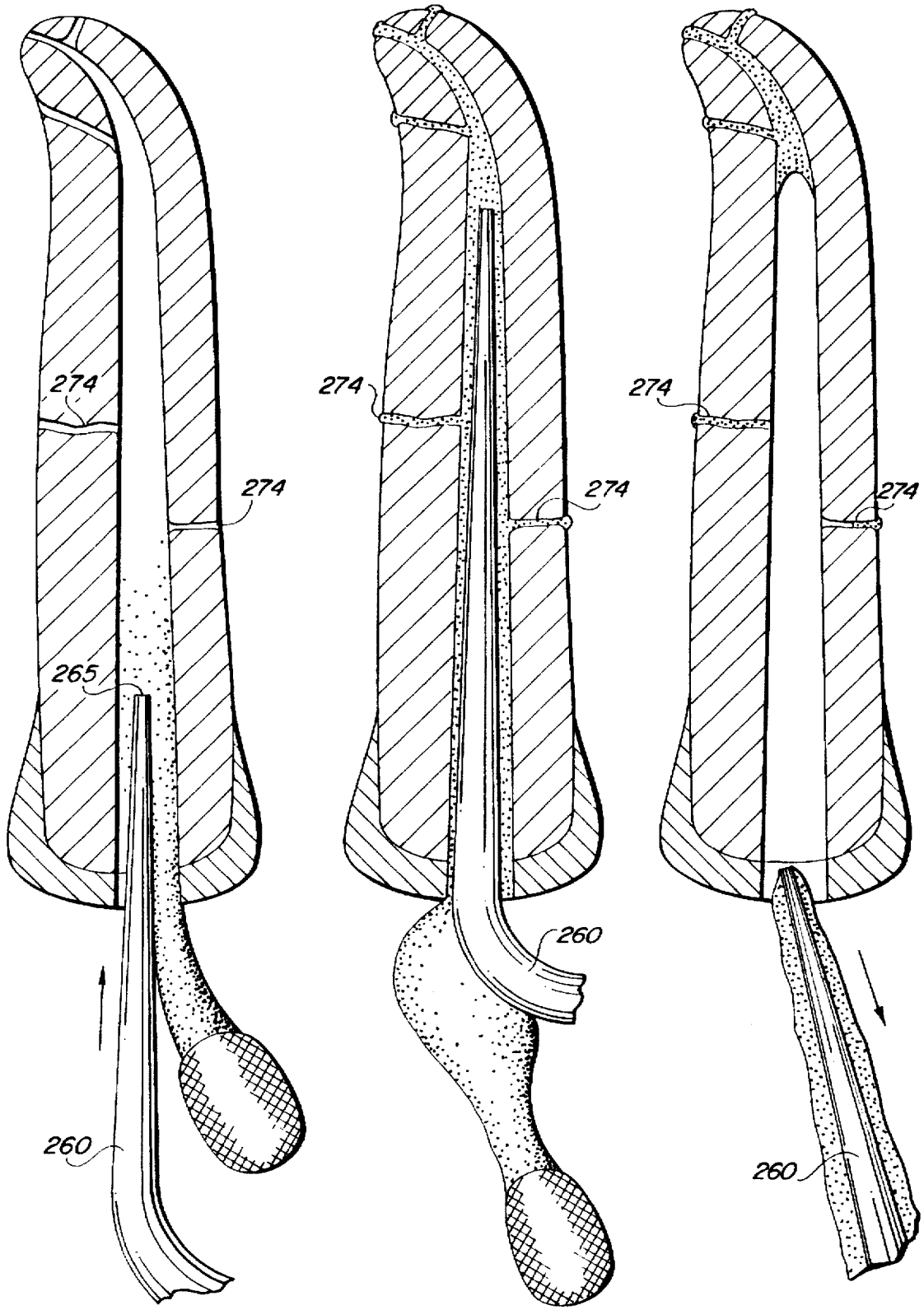

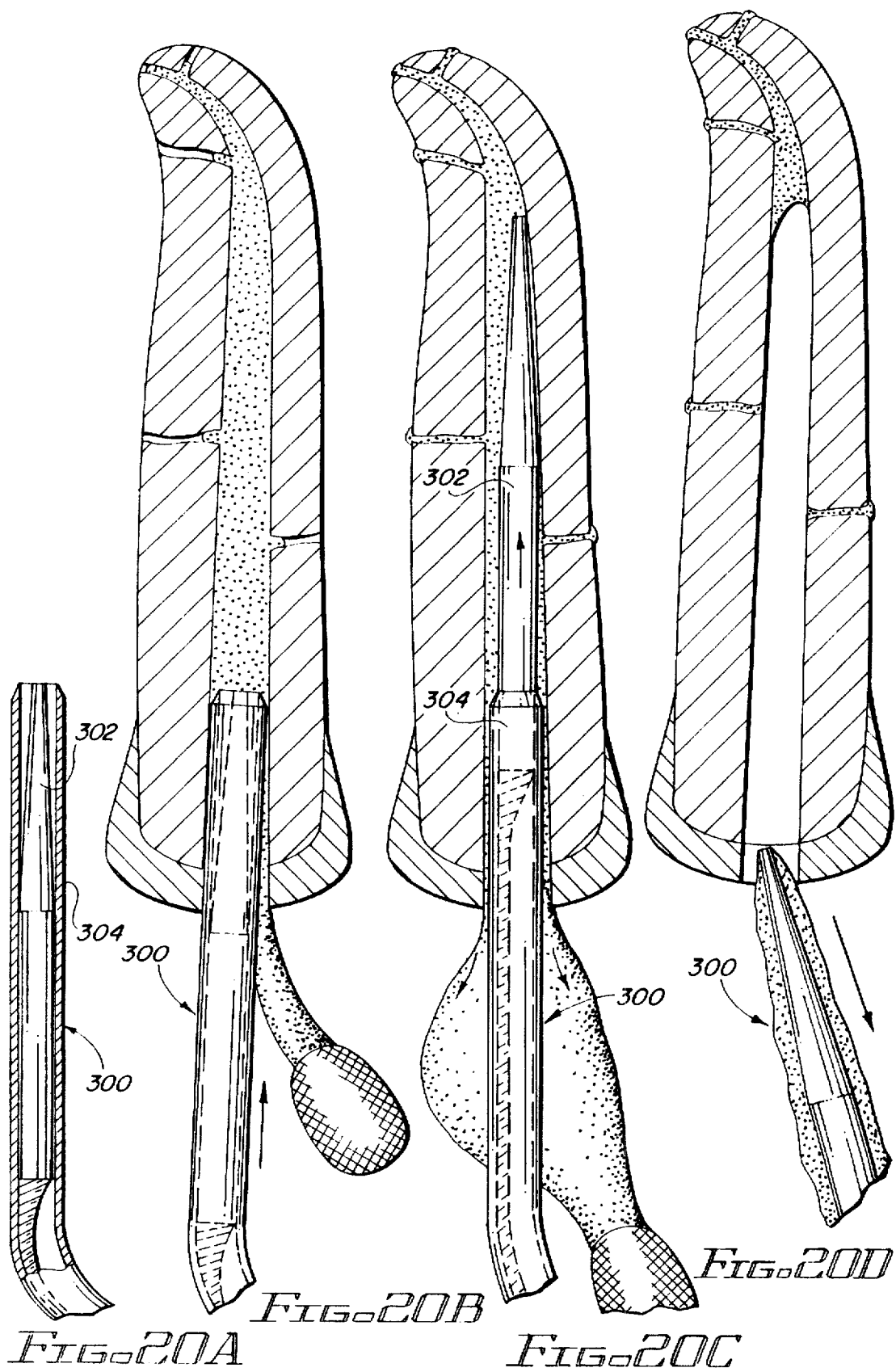

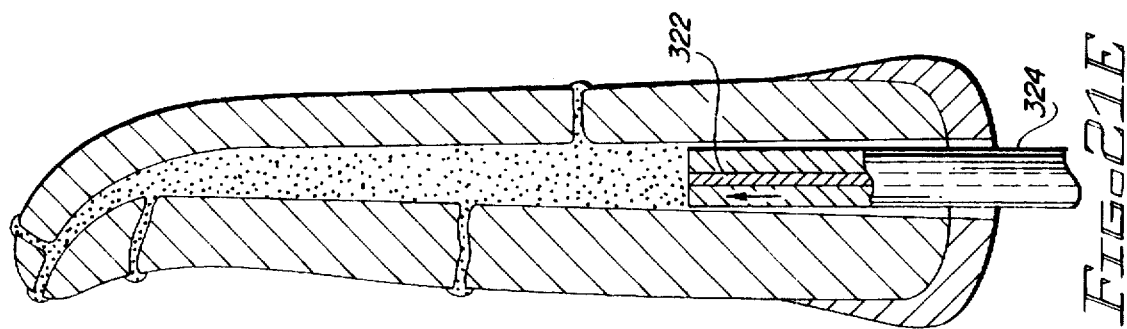
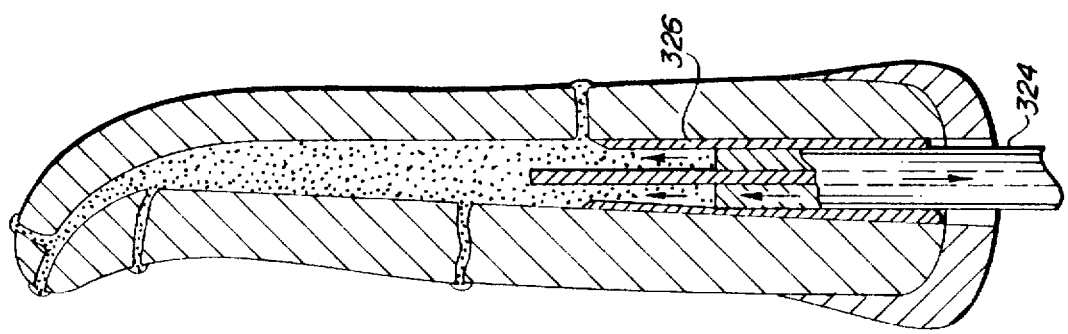
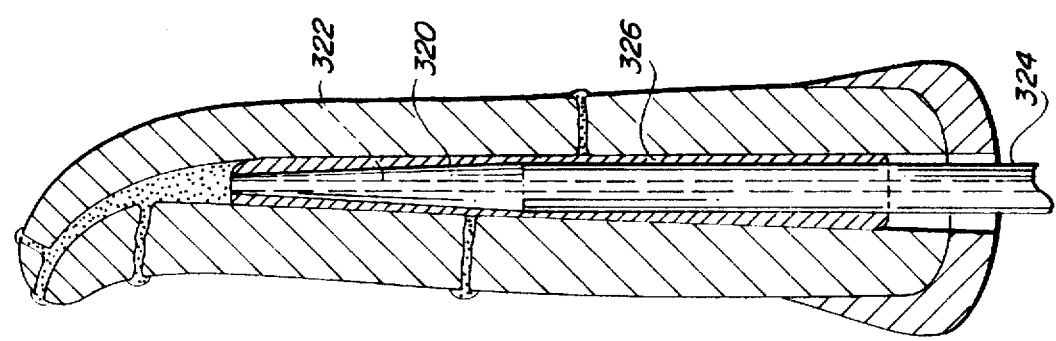
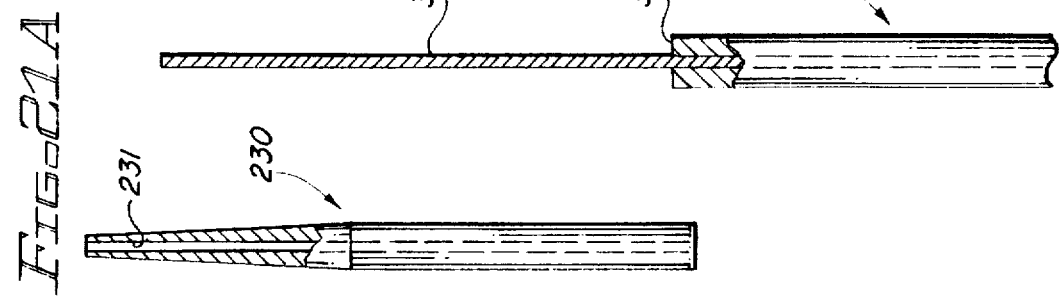

ENDODONTIC TREATMENT SYSTEM

This is a division of application Ser. No. 08/234,290 filed Apr. 28, 1994 now pending.

BACKGROUND OF THE INVENTION

1. Field of the Invention

The present invention relates generally to endodontic instruments and, more particularly, to root canal files or reamers used in the cleaning of material present in the root canal of a human tooth and for enlarging and shaping the root canal so that it may be prepared for filling and also to the materials necessary to dry, fill and restore the prepared channels.

2. Description of the Related Art

A relatively common but difficult dental procedure is the cleaning, shaping, and filling of the root canal of a patient's tooth. In the performance of a root canal procedure, a hole is first cut in the crown or exposed portion of the tooth, typically either in the biting surface of the tooth, for posterior teeth, or in the side of the tooth on the interior of the jaw for incisor teeth. Small endodontic instruments known generally as root canal files are then used to clean out the material present in the root canal, and to impart a tapered shape to the root canal so that filling material may be inserted into the root canal to seal it. An example of such an instrument, also called a broach, is shown in U.S. Pat. No. Des. 250,544 of Leonard.

Two types of instruments are in general use as root canal files, namely the K-type instrument and the Hedstrom instrument. The K-type instrument is an axially twisted and tapered, triangular or square cross-sectional shaft providing three or four spiral cutting edges along the tapered shaft and a conical tapered tip on the end thereof. An example of a K-type file is disclosed in U.S. Pat. No. 1,307,446 of Kerr. K-type files have recently come to be manufactured with lathe-cut flutes as well. The Hedstrom-type instrument is a lathe-cut file having a round tapered shaft with one, two, or three spiral cutting flutes machined into the shaft all the way to the tip. The main difference resulting from the construction of the two types of files is that the K-type file will cut in either rotational direction, or when moved up and down, while the Hedstrom-type file will cut best when moved up and down in the root canal.

When a root canal is being cleaned and shaped, a series of files having increasing diameters is used to gradually enlarge the root canal. The files are held between the thumb and forefinger of one hand by the dentist. Each file in a set of the known prior art has an identical taper from one end to the other. For example, in a typical K-type file set the taper is 0.32 millimeters on every file over the standard 16 mm length of cutting flutes, or 0.02 mm of taper/mm of flute length. This taper is sometimes referred to as a standard ISO (International Standards organization) taper. Although these file sets have identical tapers, they come in a number of sizes. The size number characterizing the file is the diameter of the file at the tip in hundredths of a millimeter, and the diameter of the file at the large end is thus 0.32 millimeters greater than this tip diameter. A complete set will include sizes 06, 08, 10, 15, 20, 25, 30, 35, 40, 45, 50, 55, 60, 70, 80, 90, 100, 110, 120, 130, and 140, while sizes 08–60 will typically be used. Some manufacturers make certain half-sizes, or off-standard sizes.

Hedstrom-type instruments similarly come in sets of increasing size, typically from 0.10 to 1.40 millimeter tip size, with 0.15–0.60 millimeter tip sizes being most commonly used. Both the K-type and Hedstrom files manufactured to ISO standards, whether twisted or lathe-cut, have flute pitches and frequencies which vary little or none in some sizes (large), but quite a bit in other sizes (small). This variation in flute angle or pitch is most perpendicular to the long axis of the file near the shank end, changing to a lessor angle (more in line with the long axis) as the flutes approach the file tip. Only one file has flute angles which vary in the opposite manner, a file disclosed in U.S. Pat. No. 4,674,979 by Jacklich, an ISO-tapered file.

The reason for Jacklich's file design is that ground-flute instruments are not strong enough or stiff enough in the smaller sizes. Ground-flute instruments have their flutes cut into tapered wire blanks which are round in cross-section. This results in the flutes being cut across the grain of the metal, thus achieving less strength than twisted-flute files. Twisted-flute files are formed by first grinding a tapering cross-sectional shape that is triangular, square, or rhomboidal down the length of the wire, in line with the metal grain. Then this tapering wire blank is twisted, causing the corners of the tapered wire blank to become spiral cutting flutes. Because of the twisting process, the metal grain is thus aligned with the helical cutting flutes.

Although stainless steel ground-flute files are of acceptable strength in ISO sizes #20 and larger, they are of inadequate strength in size #'s 06, 08, 10 and 15. In these smaller sizes only the twisted-flute instruments are stiff enough, with a short #15 file being typically used to initially penetrate coronally occluded canals. Jacklich has attempted to circumvent this problem in his ground-flute Hedstrom-type files by creating a flute pitch angle which increases as the instrument tip is approached, thereby decreasing the depth of the flute spaces and increasing the mass of metal in the more fragile tip region. While this feature does add strength to the tips of smaller ground-flute instruments, it creates file tips which are too stiff and inefficient in the larger sizes.

Unfortunately, even twisted-flute #15 files are often not strong enough to withstand the tremendous apical forces which dentists bring to bear when attempting to negotiate calcified canal orifices. As they are pressed into the pulp chamber floor in an attempt to get a "catch" in a calcified canal orifice, these ISO tapered #15 files often buckle, requiring their disposal and the use of yet another #15 file. It is typical that dentists will destroy 10–20 #15 files before they can sneak to the end of these difficult canals.

Another problem countered when using negotiation files of small diameters is the relatively large jump in tip diameter between #10 files and #15 files, a change of 50%. Schilder has addressed this problem in his U.S. Pat. No. 5,017,138 which describes ISO tapered files with tip diameters which increase proportionally in size, providing a series of files with tip sizes 0.10, 0.126, and 0.067 mm in diameter. Maillefer manufactures a non-proprietary file set with half sizes in these smaller instruments, providing clinicians with sizes 0.01, 0.125, 0.15, 0.175, etc., so that progressing between sizes #10 and #15 files is easier.

Root canals are seldom straight and there is always the possibility of causing irreversible damage to roots during shaping procedures, depending on the thinness of the root and severity and location of the root curvatures. If too large a file is advanced too far into a curved root canal, it may easily cut through the side of the root, which is referred to as a perforation of the root, and usually the tooth must then be extracted.

Another cause of root perforation is the inadvertent introduction of large engine-driven Gates-Glidden or Peezo burs into the middle third of thin, curved roots. Quite often, when these burs are new and sharp, the operator will intend to use one of the larger sizes only at the orifice of the canal but will helplessly watch the bur grab the canal walls and pull itself into dangerous depths in the root.

While perforation is probably the worst outcome of mistakes in shaping procedures, there is a more common problem in near-perforations and root weakening caused by overzealous widening of the canal preparation. It is well documented in the endodontic literature that adequate shape in the cervical two-thirds of the canal preparation is mandatory to accomplish adequate cleaning of the canal, to provide necessary control of instruments in the delicate apical regions of the canal, and to effectively obturate the whole root canal space. However, it is difficult to determine the fine line between creating adequate access and dangerous over-instrumentation, as all of these procedures are accomplished in microscopic root canal systems that are hidden from direct view.

Furthermore, if the tip of the file does not follow the curvature of the canal and bores a passage branching out from the root canal, which is referred to as ledging, surgical correction of the problem is often necessitated. It is thus apparent that the art of root canal shaping is one which requires great skill to prevent damage to the tooth and to create a tapered canal preparation conducive to ideal filling of the canal.

The technique used with a conventional set of files having identical tapers to clean and shape the root canal is referred to as the "step-back" technique. A series of file sizes from 08 to 60 (12 instruments) are introduced into the canal from smallest to largest with each successively larger file being used further back from the end of the canal. Additionally, between 4 and 6 sizes of Gates-Glidden or Peezo burs are similarly used in this step-back manner comprising a total of 16 to 18 instruments.

This technique is, at best, a difficult and time-consuming method as the dentist must indirectly gauge the rate of taper in the preparation by the distance interval of step-back of the progressively larger instruments as they fit further back from the canal terminus. As only the ISO taper of 0.02 mm/mm is currently available in standard sizes to dentists in files, irrigation cannulas, condensation pluggers, heat carriers and injection needles, paper points, filling material, and restorative posts, the current shift to canal preparations of greater taper has created great difficulties for dentists who want to enhance their root canal shaping objectives. The skills required, with these relatively non-tapered instruments and materials, to create conservative but adequately tapered shapes in root canals and to easily and ideally fill them usually comes only after treating hundreds of clinical cases.

In my prior U.S. Pat. No. 4,836,780, I disclosed a solution to this shaping problem which involved a series of tapered files with Hedstrom flutes to be used in a push-pull motion, the files having a SAFE EDGE™ or non-cutting surface along one longitudinal side of the instrument. While these variably tapered instruments can create continuously tapered root canal preparations, they are extremely difficult to pull out of the canal by hand because the whole length of the cutting flutes is engaged in the canal, as opposed to standard ISO Hedstrom files which are relatively untapered, engaging less canal length during shaping, and therefore easier to use in a push-pull fashion.

In his U.S. Pat. No. 4,536,159, Roane disclosed a new, more effective method of manipulating ISO-tapered K-type root canal files, wherein the file is lightly rotated in a clockwise direction to thread the file into the canal, after which, with apical force applied, the file is counterclockwise rotated to cut and plane the canal walls. Because the clockwise direction of the flutes causes the file to back out of the canal when it is counter-rotated, the file tip tends to center in the canal just before it cuts, if the apical force being applied to the handle is great enough to keep the file in place. In addition, Roane determined that straight ISO-tapered files can be used in curved roots without risk of perforation as long as rotary cutting motions are used and push-pull motions are avoided. Thus, aggressive rotary shaping of curved canals with unbent ISO-tapered K-type files can be accomplished without ledging or perforation of the canal walls.

While this filing motion would aid the use of variably-tapered K-type shaping files with their challenging full-length engagement of the canal walls, it became apparent during my testing that as files were given greater tapers, they became more likely to perforate curved roots, due to the increasing stiffness attendant with the larger shank diameters of the more tapered files in the series. Additionally, the standard "hour-glass" file handle disclosed in Roane's patent, while not ideal for rotary cutting techniques with ISO-tapered files, is actually inadequate, due its shape (designed for push-pull filing motions) and narrow diameter, for rotary cutting with files of greater taper. The SAFE EDGE™ feature, while eliminating lateral root perforation when using push-pull filing motions, by definition excludes the use of rotational cutting motions, as the safe-edge would then move to all surfaces of the canal, thereby negating the safety feature's function in curved roots.

Other prior art to be mentioned here is that relating to the non-standardized nature of conventional irrigation cannulas, paper points, gutta percha points, obturation carriers, obturation pluggers, heat carriers, backfillers, and restorative post systems when used in the creation and treatment of tapered root canal preparations. Existing irrigation cannulas are parallel-sided, with different designs of opening at their tips. These are used to wash the inside of root canal systems with solutions with the intention of debriding, disinfecting, and cleansing the canal space prior to sealing it. Unfortunately, these irrigating cannulas are limited in their ability to clean the ends of root canal systems as they are so small in diameter. Research to date shows that irrigating cannulas are only effective to the extent that they can penetrate the canal, usually to midroot, leaving the important apical third of the canal unaffected.

Dentists are able to overcome this problem by the use of small patency files which are used to clear debris from the end of the canal, but which also displace irrigant from this apical region of the canal during its use, allowing fresh irrigant back into the apical region after the file's withdrawal. As the files are relatively untapered (ISO 0.02 mm/mm) this irrigant exchange is limited.

When the canal has been cleaned and shaped, it is dried with absorbent paper points of varying size and taper. In canals which have been tapered with burs and files in a step-back fashion, it is often necessary to use several different sizes of paper points to dry the whole length of the canal, small paper points apically, larger paper points for the middle of the canal, and sometimes even larger paper points for the cervical region of the canal. Furthermore, as the tapers of the paper points seldom match the taper of the canals, there may be moisture left on parts of the canal walls after drying procedures.

There are several methods of sealing root canal systems, most of them using a rubber-like material called gutta percha. When used as a tapered gutta percha cone, this material is compacted into the canal with pluggers, or the gutta percha material may be placed as a coating on an obturating carrier, which is warmed to soften the gutta percha and placed in the canal, with the carrier compacting the material into the canal space.

Currently, the shapes of filling materials and obturating carriers do not match the tapering shapes of prepared canals either. When the step-back technique of canal shaping is used, the final shape of the canal preparation can only be discerned indirectly, by the increments that each larger instrument fits further back from the terminus of the canal, a difficult skill learned only after much experience. As the prepared taper is often obscure to the clinician, it is likewise difficult to pick an appropriately tapered gutta percha point or obturating carrier with which to seal the canal. If the selected obturating device or gutta percha point is too tapered, they will bind in the canal short of its terminus, causing the crucial apical seal to be inadequate, allowing leakage and failure of the endodontic treatment. If the obturating carrier or material is too narrow, little hydraulic pressure will be exerted on the filling materials in the cervical two-thirds of the canal during condensation procedures, and lateral or accessory canals in that region of the canal may not be sealed, again increasing the chance for failure of treatment.

While there are many techniques of filling root canals, it is generally recognized in the field of endodontics that those methods which warm and soften the gutta percha filling material, allowing it to be thoroughly compacted into all the nooks and crannies of root canal systems, are superior to those techniques which do not thermoplasticize the gutta percha prior to condensation.

The classic technique was described by Schilder in 1969, vertical condensation of warm gutta percha. In this technique an appropriately tapered gutta percha cone is fit and cemented in the prepared canal, after which a flame-heated or electrically-heated gutta percha heat carrier is used to sear off the gutta percha cone at the orifice level of the canal. By pressing the softened gutta percha into the canal with an appropriately sized vertical condensation plugger, the first wave of condensation is initiated, filling any lateral canals present in that region in the primary canal. The heat carrier is then reintroduced into the canal, penetrating the gutta percha several millimeters, heating the apical mass, and removing a portion of it so that the next wave of condensation may occur deeper in the root. These heating and compacting cycles continue until the final wave of condensation which ends 5–7 mm from the canal terminus.

Typically it takes 3–7 waves of condensation to reach this end point. At this point the clinician must either place a retentive post in the coronal canal space or backfill it with gutta percha. Backfilling can be done by heating 3–8 small pieces of gutta percha and sequentially packing them into the canal, or by syringing alloquates of pre-heated gutta percha from a gutta percha gun and compacting them with pluggers. Downpacking with multiple waves of condensation and backfilling in the manners described require at least 7–10 different instruments, fairly extensive training of the dentist and chairside assistant, and 15–30 minutes of clinical time. Furthermore, these condensation pluggers and heat carriers lack a correlating mechanism to match their sizes to the taper of the canal preparation.

SUMMARY OF THE INVENTION

The disadvantages and limitations of the background art discussed above are overcome by the present invention. The present invention differs significantly and advantageously from the cleaning, shaping and filling technology discussed above in nine respects.

First, rather than using a large series of files of differing sizes but the same taper, as is the case when using standard ISO-tapered files, the present invention often allows full root canal shaping to be accomplished with as little as a single file from its set of variably-tapered shaping files.

Second, instead of indirectly creating a tapering canal preparation with the difficult and time-consuming serial step-back shaping technique necessary with ISO-tapered files, the present invention requires only that the shaping file or files be worked to the terminus of the canal, thereby completing the preparation.

Third, the present invention provides for variably-tapered negotiation files, allowing optimally varied stiffnesses as the tips of the instruments in the series increase in diameter. Furthermore, these files of increasing taper have small, even increases in tip diameter allowing more passive negotiation to the terminus of constricted canals.

Fourth, increasing tapers of these files can be used without increasing risks of root perforation or weakening, by progressively shortening the cutting flute length as the files become more tapered.

Fifth, one version of these tapered files can be efficiently used with rotary cutting motions without increased breakage, due to their varied flute pitch and sharpness along the length of the instruments.

Sixth, safe function of these files in curved canals is also gained through the use of nickel-titanium (Nitinol™), an alloy which exhibits extreme flexibility and elastic memory.

Seventh, the present invention differs significantly from prior art in the pear-like shape of the file handles, a design which enhances the application of pushing and rotational forces to the file by the dentist's fingers.

The eighth improvement over existing art is the provision of irrigating cannulas, paper points, filling materials and instruments, and restorative posts which are contoured to match the pre-defined canal preparations created by the variably-tapered shaping files, thereby matching corresponding ones of the shaping files.

Ninth, the present invention includes a technique whereby canals can be more simply ideally obturated in all their complexity with the aforementioned tapered filling instruments and materials used in a single inward wave of condensation, followed by a single backfilling wave to complete the fill if a post is not to be placed in the canal.

With regard to the first two features of the present invention, several advantages over the art are achieved by using variably-tapered files. The purpose of endodontic shaping procedures is to create a continuously tapering preparation which is narrowest at the end of the canal, and widest near the crown of the tooth. By using files that vary in their tapers, it has been determined that root canals may often be prepared by using a single shaping file instead of the 16 to 18 files required by conventional ISO-tapered instruments. While it is readily apparent that the use of only one tool instead of 16 to 18 tools is desirable from a standpoint of efficiency, it should also be noted that the present invention provides ideal root canal shaping results with less training and experience. Rather than creating a tapered canal shape by the difficult and time-consuming step-back technique, the present invention simply requires that a shaping instrument of appropriate taper be worked to the full length of the canal. In addition to the greatly improved ease and simplicity of shaping canals with a single instrument, this provides, for the first time, a pre-defined shape throughout the full length of the canal. One of the most important advantages provided by pre-defined root canal preparations is the resultant ability to optimize cleaning and filling procedures in root canal systems. Since the design of files taught by the present invention involves different tapers, the tips of the shaping files are not used to cut a path in the canal as in files with standard tapers. Whereas standard ISO file sets have the same tapers but increasing tip diameters in the sequence of files, the tip diameters of a set of shaping files constructed according to the present invention may be the same between files of different tapers. There may also be different sets of these shaping files which differ in their tip diameters, i.e. one set of shaping files with tapers of 0.04, 0.06, 0.08, 0.10, and 0.12 mm/mm and the same 0.2 mm tip diameters; another set of shaping files with the same range of tapers but with 0.35 mm tip diameters, etc. And finally, the present invention includes sets of shaping files with similar non-ISO tapers which vary by evenly or proportionally increasing tip diameters.

The third difference in the present invention is the provision for variably-tapered negotiation instruments with even or proportional increases in tip diameters. This file set has tapers which range from 0.1 mm/mm to 0.5 mm/mm, thereby imparting twice the usual stiffness in the critical initial negotiation file with a 0.15 mm tip diameters. After the canal has been penetrated to midroot by the rigid 0.04/0.15 (taper/tip diameter), the dentist can either progress downward in size to the 0.03/0.125, the 0.02/0.10, and finally the 0.01/0.075 or drop down to the 0.01/0.075 taken to full length and then work up in the file sizes until the 0.04/0.15 goes to length. When the files of narrower taper are embedded at least halfway into a canal, the canal walls will then support narrower less robust file sizes and prevent them from buckling. Therefore this set of negotiating files should kink less upon initial entry, and provide greater tactile awareness and control of instruments in the tortuous apical regions of canals. Additionally, the 0.025 mm increases in tip size circumvent the problematic 50% jump in tip diameters between ISO-standard file sizes #10 and #15. Progressing to full length in constricted canals with this negotiating file set, from sizes 0.075 mm to 0.10 mm to 0.125 mm to 0.15 mm, is effortless as a result.

The fourth important difference between the present invention and the art is that shaping files constructed according to the teachings of the present invention can be safely used in curved canals and/or thin roots in spite of their greater rates of taper. This is accomplished very effectively by the specification of progressively shorter flute lengths as files in a set have progressively greater tapers, thereby limiting their maximum flute diameters. Without this feature, the shank-end flute diameters of variably-tapered shaping files become wider and stiffer as the tapers of these instruments increase, and their potential for lateral perforation or weakening of the root increases as well.

While limiting the maximum flute diameter of these increasingly tapered shaping files allows their safe use, this feature is extremely important in a broader sense. Using a single shaping file instead of the usual 15–18 instrument set means that the final shape through the full length of that canal is pre-defined, unlike the shaping result when six different sizes of Gates-Glidden burs are used progressively shallower in the coronal portions of the root canal. It is extremely common for Gates-Glidden and Peezo burs to be used too deeply in thin roots, risking weakening and perforation. Simply limiting the maximal flute diameters of shaping files allows, for the first time in the field of endodontics, enlargement of the coronal two-thirds of a canal to an extent that is exactly adequate to clean the tiny apical regions of the canal and to maintain control of shaping and filling instruments in that region, but not a bit larger. The present invention includes this feature applied to the variably-tapered Hedstrom-flute shaping file shown in my U.S. Pat. No. 4,836,780 and to all other types of shaping instruments as well, whether they are used by hand or with sonic, ultrasonic, or mechanical handpieces.

Fifth, safety and efficiency when these shaping files are used with rotary cutting motions is gained in the present invention by longitudinally varying the pitch and relative sharpness of cutting flutes. When shaping files are used with rotary cutting motions two primary problems are encountered, potential for breakage and slowness of cutting. This is overcome in the present invention by varying the flute pitch from an in-line reamer-like angle at the shank end of the instrument to a more perpendicular K-type flute angle at the file tip. Instead of, or in addition to the above, the relative sharpness of the cutting flutes is varied along the length of the files, being sharpest at the strong shank end to allow for aggressive cutting by the wider flutes, and dullest near the smaller, more fragile tip of the file so these flutes can easily release from the canal wall during rotation, thereby preventing file breakage which can occur when the tip binds.

Sixth, functional safety when using tapered shaping files in curved canals is enhanced through the use of the alloy nickel-titanium (Nitinol™. This unusual metal exhibits stress-induced phase-transformation of its crystal lattice structure resulting in characteristics of superelasticity, allowing large-diameter Nitinol files to work around root canal curvatures that would be impossible with stainless steel. Nitinol's elastic memory also allows, in one arrangement of the invention, curvatures to be preset in the file during the manufacturing process. By heating and cooling files made of this metal, different curvatures can be present in the metal so that the desired shape is "remembered", allowing the file to straighten in the relatively uncurved coronal portion of canals and recurve itself when the file tip moves deeper and encounters apical root canal curvatures. When added to a Hedstrom-fluted taper file, a preset file bend directed toward its safe edge causes the Nitinol version of this shaping instrument to automatically seek the inside of canal curvatures with its non-cutting side, thereby effortlessly preventing lateral perforation.

The seventh aspect of the present invention involves an improvement in the shape of the handle provided for files of the invention. Standard file handles conventionally have a narrowed waist portion with enlarged diameters at both ends of the handle. This is to accommodate a push-pull action in conventional use of the file. Handles in accordance with the present invention have an end diameter smaller than the waist of conventional file handles, and they taper to a larger-than-conventional diameter near the file shank, where the file is embedded in the handle. Since the file is designed to cut with apically directed rotary forces, the shape of the handle enhances operator comfort and reduces the force necessary to cut the desired shape into the root structure around the original canal. This "pear-shaped" handle also enhances the use of standard ISO K-type files used with apically-directed cutting motions.

Eighth, one of the most important improvements over existing art is the provision of a coherent system of irrigating cannulas, paper points, filling materials and instruments, and restorative posts which relate to the shapes of corresponding shaping files and thus to the pre-defined canal shapes created by these tapered files. Specific and isolated improvements in root canal preparation and filling techniques often create more procedural problems than they solve, as clinicians must somehow fit this new technique nuance into their usual procedural flow. The present invention incorporates an integrated system of variably-tapered shaping files and similarly-tapered implements and materials, which work together. Any canal which has been shaped by an 0.06 mm/mm tapered shaping file can, without further thought, be cone-fit, dried, obturated and restored with instruments and materials manufactured to the same shape, thereby enhancing the safety, ease of use, and results of the clinical practice of endodontics.

Finally, the present invention includes an obturation technique which utilizes variably-tapered electric heat pluggers to downpack and backfill root canals in single waves of condensation, dramatically reducing the technical complexity and number of instruments needed over the traditional Vertical Condensation of Warm Gutta Percha Technique. There are two embodiments of this invention which are useful, one to be used in canals shaped and cone fit by traditional means, the other to be used in the pre-defined preparations created by variably-tapered shaping files. In the first instance, serial step-back instrumentation procedures are used to impart a tapered shape to a given canal after which a non-standardized gutta percha cone is fit in the canal and cemented with sealer after the canal is dried. Instead of using a standard untapered electric heat carrier, 5 pluggers, and 4–5 waves of condensation as needed in the Vertical Condensation of Warm Gutta Percha technique, the Continuous Wave of Condensation technique requires only a single tapered electric heat plugger and a single movement of the heat plugger through the pre-fit gutta percha cone to accomplish the same quality of result. The key to this technique is that the electric heat carrier is used as a plugger, and the heat pluggers in this set have the same shapes as the non-standardized gutta percha points which are fit in tapered canal preparations. Generally speaking, clinicians fit gutta percha points with slightly less taper than the root canal preparation, therefore a heat plugger with the same taper as the gutta percha point will by definition fit that canal shape.

In the other embodiment of the present invention, the electric heat pluggers have the same or nearly the same configurations as the variably-tapered shaping files. This can provide a more ideal obturation result as canal shapes are more precisely controlled throughout their length with this shaping method, therefore insuring a more precise match of canal shape and heat plugger. Because of this close fit of these pluggers to the pre-defined canal shapes the hydraulic pressures exerted on the thermosoftened gutta percha and sealer cement are more effective in their ability to fill lateral and accessory canals off the primary canal. As the heat plugger is moved through the recently softened gutta percha, it eventually binds the canal short of its terminus and the downpack is completed. The tip diameter of the heat plugger determines this apical endpoint of the downpack and it is chosen to terminate 3–5 mm from the canal terminus.

In the second part of this filling technique, there are pre-formed gutta percha backfilling plugs, which match the vacant space left after the downpack is completed, and a different electric heat carrier/plugger device with which to heat soften and compact the backfilling plug into the coronal aspect of the canal. In preparation, the narrow heat carrier tip is extended beyond the plugger tip and is inserted into a groove or passage in the backfilling plug after which a short burst of heat fuses the plug to the backfilling device. The device with its attached gutta percha plug is then placed cold into the empty canal region and, as a heating cycle is initiated, the heat carrier tip is withdrawn from the plug as the plugger is simultaneously used to push the recently softened plug into the canal space.

BRIEF DESCRIPTION OF THE DRAWINGS

A better understanding of the present invention may be realized from a consideration of the following detailed description, taken in conjunction with the accompanying drawings in which:

FIG. 1 is a somewhat schematic view of a root canal in a tooth, with a portion to be removed during root canal shaping procedures shown in broken lines;

FIG. 1A shows a conventional K-type file;

FIG. 2 is a schematic representation indicating the final intrusion of the tips of each of eleven conventional files into the root canal of FIG. 1, illustrating the conventional step-back technique;

FIG. 3 is a schematic view of the conventional file of FIG. 1A being used to clean and shape the root canal, and specifically illustrates both the perforating and ledging of the root canal;

FIG. 3A is a view like FIG. 3 except that it illustrates the damage which may result from misuse of a Gates-Glidden bur;

FIG. 4 is a schematic view showing one of a series of variably-tapered implements in accordance with the present invention;

FIGS. 4A and 4B are schematic views illustrating two different flute-to-shank transitional configurations of the implement of FIG. 4 designed to eliminate gouging of curved canal walls by the large shank-end cutting flutes;

FIGS. 4C through 4E are schematic views illustrating different cross-sectional flute designs of the implement of FIG. 4 which vary the sharpness and cutting efficiency from the tip (dullest) to the shank (sharpest) in order to decrease the chances of breaking the tips of files when the flute near the tip grabs the canal wall;

FIG. 4F is an elongated schematic view of the radiused file tip of the implement of FIG. 4 showing tapering lands which blend into the fully-sharp cutting flutes slightly back from the end of the file;

FIG. 4G is a schematic view showing one of a series of variably-tapered files of the present invention wherein the helical cutting flutes spiral in the reverse, or counterclockwise direction to allow apically-directed cutting to be accomplished with a clockwise rotary motion;

FIG. 4H is a schematic view showing the shank end of one of a series of shaping files of the present invention with a latch-grip shank for use of the file in a slow-speed handpiece instead of a handle to be grasped with clinician's fingers;

Figure 12A:
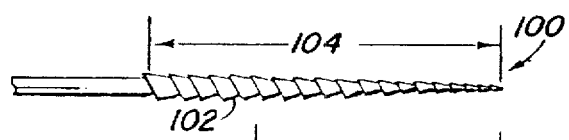
Figure 12B:
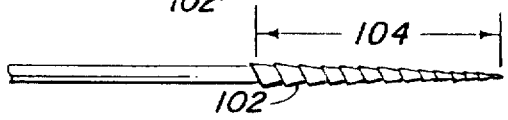
Figure 12C:
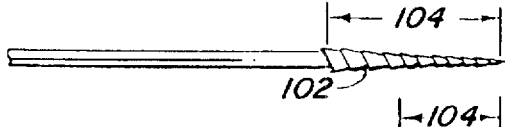
Figure 12D:
Figure 13A:
Figure 13B:
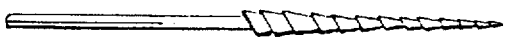
Figure 13C:
Figure 13D:
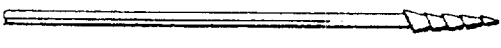
Figure 14A:
Figure 14B:
Figure 14C:
Figure 14D:
Figures 17F, 17G, 17H, 17I:
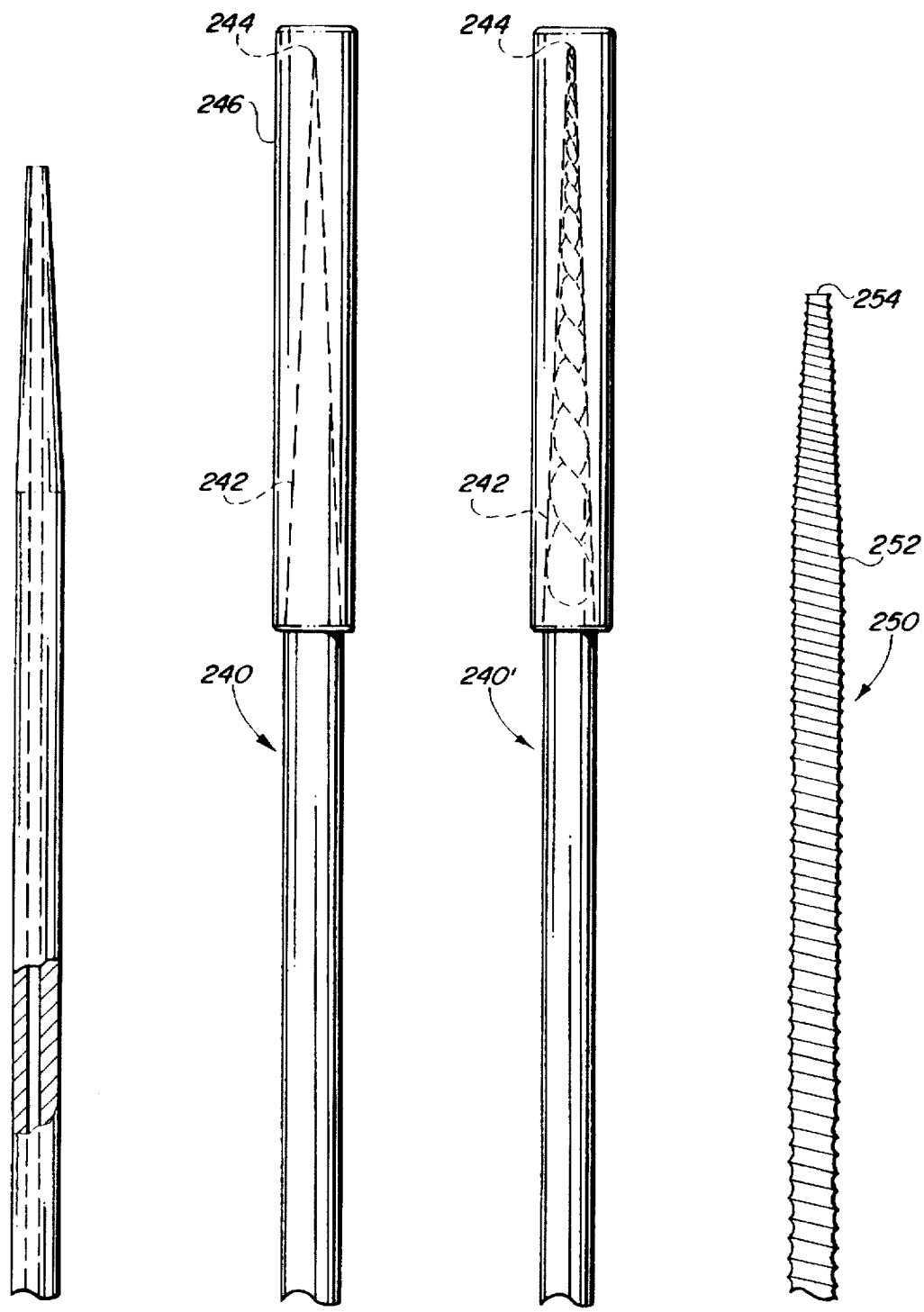

Views A and B of FIG. 5 are schematic views illustrating a set of standard ISO-tapered files, each equipped with a handle in accordance with the present invention;

FIGS. 6A through 6C are schematic views illustrating the potential for the gouging of curved canal walls with a terminal shank-end flute (FIG. 6A), and two variants of my design which will eliminate gouging and maintain smooth continuous canal preparations;

FIG. 7A (1–4) is a schematic view of four implements making up a set constructed in accordance with my prior U.S. Pat. No. 4,836,780, but with handles corresponding to my present invention, wherein files of varying taper have similar flute lengths and increasingly greater maximal flute diameters;

FIG. 7B (1-4) is a schematic view of four implements making up a set constructed in accordance with the present invention, with each file of greater taper having progressively shorter lengths of cutting flutes, thereby limiting the maximum diameter of the canal preparation regardless of the length and extent of taper;

FIG. 8A is a schematic view of a molar with files from FIG. 7A, showing the potential for lateral perforation of roots with variably-tapered files having similar flute lengths;

FIG. 8B is a schematic view of a molar tooth and files from FIG. 7B, showing the advantages of shorter flute lengths with greater file tapers;

FIGS. 9A-9C are schematic views illustrating a set of three files of the same taper, but with increasing shank diameters and the different flute lengths which result;

FIGS. 10A and 10B are schematic views illustrating the appropriate use of the files of FIG. 9 in roots of different diameter;

FIGS. 11A, 11B and 11C are schematic views illustrating the serial use of different files of FIG. 9 to sequentially enlarge a single canal;

FIGS. 12A-12D schematically illustrates a set of variably-tapered Hedstrom files with safe edges as disclosed in my prior U.S. Pat. No. 4,836,780, but with flute lengths which become shorter as the file tapers become greater;

FIGS. 13A-13D schematically illustrates a set of ISO-tapered Hedstrom files with flute lengths becoming progressively shorter as the tip diameters become greater;

FIGS. 14A-14D schematically illustrates a set of variably-tapered K-type files with flute lengths which become shorter as the file tapers become greater;

FIGS. 15A-15D schematically illustrates a set of files with a single non-ISO taper with flute lengths becoming progressively shorter as the tip diameters become greater;

FIG. 15E is a schematic view of one of a set of "U" files configured for use in a handpiece, with FIGS. 15E-1, 15E-2 and 15E-3 showing the cross-sections at different points in the file;

FIG. 15F-1 through FIG. 15F-5 are schematic views of a set of negotiating files of different tip diameters, different tapers and equal flute lengths;

FIG. 16 (views A through F) are schematic views illustrating the formation and function of preset curvatures in nickel-titanium root canal files;

FIG. 17 (views A through I) are schematic views illustrating a particular set of elements of the Buchanan Endodontic Treatment System;

FIGS. 17A and 17B are schematic views illustrating non-ISO tapered files with clockwise and counter-clockwise flute direction;

FIG. 17C is a schematic view illustrating an irrigating cannula with a taper matching the taper of the shaping files in FIGS. 17A and 17B;

FIGS. 17D and 17E are schematic views of paper canal drying points and gutta percha filling points, respectively, with tapers matching the taper of the shaping files in FIGS. 17A and 17B;

FIG. 17F is a schematic view illustrating an electric heat carrier/condensing tip with a taper matching the taper of the shaping files in FIGS. 17A and 17B;

FIGS. 17G and 17H are schematic views illustrating plastic and metal gutta percha filling carriers with tapers matching the tapers of the shaping files in FIGS. 17A and 17B;

FIG. 17I is a schematic view illustrating a retentive restorative post with a taper matching the taper of the shaping files in FIGS. 17A and 17B;

FIG. 18A is a side elevational view of an improved heat carrier/plugger in accordance with my invention;

FIG. 18B is a schematic representation of the heat carrier/plugger of FIG. 18A in two different versions corresponding to two different versions of gutta percha points;

FIG. 19 (views A, B and C) represent the use of the heat carrier/plugger of FIG. 18A in packing gutta percha material into a root canal;

FIG. 20 (views A through D) are schematic views illustrating a tapered heat carrier/plugging tool as it is used to soften and downpack through a prefit gutta percha cone in a continuous wave of condensation, sealing the root canal system; and FIG. 21 (views A through E) are schematic views illustrating a backfilling device, the associated backfilling gutta percha plug, and its heating and compaction into the coronal two-thirds of the root canal.

DETAILED DESCRIPTION OF THE PREFERRED EMBODIMENTS

Before describing the present invention, it may be helpful to discuss briefly the root canal procedure as shown in FIGS. 1-3. FIG. 1 shows a tooth 10 located in the bone 12 of a jaw. The tooth 10 in FIG. 1 is an incisor, and the opening in the crown of the tooth 10 is cut on the side of the tooth 10 in the interior side of the jaw (not shown), which opening is generally indicated at 14. The tooth 10 has a nerve canal 16 extending to the tip of the tooth 10 which is embedded in the bone 12.

Also shown in FIG. 1A is a K-type file 20, having a handle 22 supporting the file 20. The file 20 has a flute length X, a shank diameter Y, and a tip diameter Z. In a standard file of this type, X=16 mm, Y=0.32 mm and Z varies with the size of the file, beginning with 0.06 mm for the smallest file and increasing to 1.4 mm for the largest files. The file 20 has a sharp tip 24, which is needed since each successive file in a series has a larger diameter at the tip. It should be noted that, while the discussion of the prior art uses as an example a K-type file, it is equally applicable to other configurations of like-tapered root canal file designs.

Referring now to FIG. 2, the file 20 is shown inserted into the root canal 16, which is enlarged from the view shown in FIG. 1. With conventional files, the step-back technique discussed above is used, with each progressively larger file being inserted shallower and shallower into the root canal 16. The numbers along the root canal 16 near the tip end of the root canal 16 represent the maximum extent to which different size files are inserted, with file sizes from 10 to 60 (representing tip diameters from 0.10 mm to 0.60 mm) being used. As mentioned above, a minimum of nine to eleven files are required, with 15 to 17 instruments more frequently being necessary.

Referring next to FIG. 3, the file 20 is shown inserted into a root canal 30 in a molar tooth 32. As is apparent, for the molar tooth 32 a hole 34 to admit the file 20 is present in the biting surface of the tooth 32. Since the file 20 was too large and not curved enough, it has perforated the curved root canal 30 at the location indicated by the reference numeral 36. As mentioned above, perforation can also occur when the file 20 is not pulled against the outside curve of the root canal 30 by using the anti-curvature motion discussed above.

Another problem shown in FIG. 3 is that the tip 24 of the file 20 has left the root canal 30 and cut a ledge along the outside curvature of the root canal 30. Succeeding files may well become trapped in the ledge also, and will not properly clean and shape the root canal 30. The present invention eliminates both perforation and ledging of a root canal, and in addition makes the root canal operation quicker and easier to perform.

FIG. 3A illustrates a similar problem which may be encountered when using an engine-driven bur. As in FIG. 3, FIG. 3A depicts a molar tooth 32 with a root canal 30 accessed by a provision of a hole 34. Instead of the file 20, a Gates-Glidden bur 37 is shown working in the root canal 30, driven by a power head 38. As is shown in FIG. 3, the bur 37 has perforated the curved root canal 30 at the location indicated by the reference numeral 36.

FIG. 4 shows a tapered shaping file 50 in accordance with my invention having a handle 52 in which is affixed a shank 54 terminating in a working portion 56. The handle 52 has a hole 58 extending through it near the proximal end for the insertion of a safety retraction loop. As indicated, the shank 54 has a diameter A which is slightly less than the maximum diameter B of the first flute 62, with transitional lands 66 extending between the first flute 62 and the smaller diameter file shank 54. The working portion 56 comprises a plurality of flutes 60, each being provided with cutting edges about the periphery, diminishing in diameter and sharpness and increasing in pitch with distance from the first flute 62. The tip 64 is smooth, without any cutting edge, and has a diameter C which is slightly smaller than that of the last flute 60 which transitions by the land 65 to the tip 64 (FIG. 4F).

While any or all of the shaping instruments described in the present invention may be mounted in a latch-grip shank 81, as seen in FIG. 4H, and operated in a dental handpiece, FIG. 4 shows the handle 52 of my preferred embodiment, formed in the shape shown between two opposed planar surfaces 76 and 84. These planar surfaces are 2 mm in diameter. From the boundary of the surface 76, the handle enlarges through a smooth curved region 78 to its maximum diameter of 6 mm at the point 80. In a section 82 between the maximum diameter 80 and the proximal end 84, the handle tapers linearly and is scored all around with a plurality of tapered grooves 83. The transverse plane at the maximum diameter 80 is spaced 2 mm from the planar surface 76 and the distance between the plane of the maximum diameter 80 and the proximal end 84 is 8 mm, the overall length of the handle 52 being 10 mm. The grooves 83 and the shape of the scored, tapered section 82 provide an enhanced gripping area for the user's thumb and fingers to facilitate applying torque to the file as it is moved into the root canal toward the apical region. The shape of this handle 52 is to be contrasted with the shape of the handle 22 in the conventional file 20 of FIG. 1A which is designed for push-pull cutting and ¼ turn-pull cutting motions, rather than apically-directed counterclockwise rotary cutting action.

The embodiment as shown in FIG. 4 has a diameter B equal to 1.0 mm, whereas the dimension A, the diameter of the shank 54, is 0.95 mm. By providing the shank with a slightly smaller diameter A than the diameter B of the first flute 62, binding of the file shank in a root canal is avoided. However, if the diameter of the shank 54 is too much smaller than the diameter of the first flute 62, the file may be weakened at that transitional point, and the largest shank-end flute may transport the original path of the canal, as seen in FIG. 6A. The transitional lands 66 seen in FIGS. 4A and 6B extending from the first flute 62 to the shank 54 help to guide the file in the root canal and limit divergence of the first flute from the preparation path.

FIG. 4B shows an alternate embodiment with a shank guide 68 which is separate from the cutting flutes of the file. This shank guide embodiment is separated from the largest flute by a distance 69 which allows a chip space for tooth dust to collect after it is cut from the canal walls during filing procedures. The shank guide diameter is only slightly smaller than the largest flute diameter 62 of a given file, so that it may guide that largest cutting flute without binding the prepared canal wall as the instrument progresses deeper in the root as seen in FIG. 6c.

In FIG. 4 the angle of the flutes relative to the longitudinal axis of the shank varies along the length of the files as is apparent from a comparison of the angle $\alpha$, indicated by the broken line 70, with the angle $\beta$, indicated by the broken line 72. Thus the flute angle near the larger diameter shank end is reamer-like, while the flute angle at the file tip is more like a K-file flute angle.

This flute design answers two critical challenges encountered when using a single shaping instrument to create a canal shape previously imparted with from 15 to 18 conventional instruments. Optimal function of this type of instrument requires enhanced cutting efficiency and flexibility at the larger shank end, and maximal strength at the more fragile file tip. Fortunately, tapered canal shaping objectives require less dentin removal apically: therefore the optimal tapered shaping file design can sacrifice apical cutting efficiency for added strength. The K-type flute angle provides this.

In this embodiment, the flute pitch is 0.5 flutes/mm (one flute in two millimeters) adjacent the largest diameter flute 62 and two flutes/mm or four flutes in two millimeters adjacent the tip 64. The ratio of flute pitch at the shank to flute pitch at the tip (the overall flute pitch ratio) is four in the FIG. 4 embodiment. The flute pitch ratio, defined as the flute pitch at any point along the working portion of the file relative to the flute pitch at the tip, diminishes linearly along the length of the working portion of the file. Thus, in the embodiments of FIGS. 4A–4E the flute pitch ratio diminishes linearly from four at the shank to one at the tip. Other ratios may be selected for other file sets, if desired, but a linear decrease in flute pitch ratio from shank to tip is preferred.

Similarly, the sharpness of the cutting flutes may be decreased from shank to tip, decreasing the chances of a cutting flute near the tip catching in a canal wall which easily causes file breakage when the file is used in a rotary cutting motion. The result is increased cutting efficacy near the shank end flutes where more dentin removal is needed and where the file has its greatest diameter and strength. This variable dulling may be accomplished by a number of means, including an increasing "U" blade as taught in the Arpaio, Jr., et al U.S. Pat. No. 4,934,934 (see FIG. 4C), a progressive flute edge radius as seen in FIG. 4D, or a different flute rake angle as seen in FIG. 4E.

FIG. 4F shows an enlarged view of the file tip. The file tapers to a blunt or radiused tip 64. As the slightly-smaller blunt tip blends into the cutting flutes of the file, the non-cutting tip transitions into lands 65, and finally into fully-sharp flutes 60. The blunt tip prevents apical ledging and the transitional lands prevent transportation of the apical canal path during shaping procedures. These are important features when using a single file to create the full canal shape, as the aggressive more-coronal dentinal cutting decreases the clinician's tactile awareness of file tip function. As described below, file tip diameters may be consistent between sizes of file tapers, or may vary between file taper sizes.

FIG. 4G shows the files in FIGS. 4 and 4F with cutting flutes 57 spiralling in reverse direction to aid the use of apically-directed counter-rotary filing. As most dentists use their handpieces in the clockwise direction and are used to filing in a clockwise direction, the reverse flute direction shown in this embodiment allows clinicians to rotate their handpiece files or hand files in the clockwise direction they are used to and still gain the advantages of apically-directed counter-rotary filing motions.

FIG. 4H shows the files 50 in FIGS. 4 and 4G mounted in a latch-grip slow-speed handpiece attachment 81, although these files may be effectively powered by mechanical, sonic or ultrasonic handpieces with any type of handpiece attachment including various finger handles 22 and 52 in FIGS. 1A and 4, respectively, which may be accepted by specifically designed endodontic handpieces.

Views A and B of FIG. 5 are schematic views illustrating a set of two standard ISO-tapered files 20, each equipped with a handle 52 in accordance with the present invention. With the advent of the Balanced Force cutting motion for root canal instruments, clinicians are no longer pulling files out of canals to cut dentin. Using this counter-clockwise cutting motion the files are only directed into the canal during dentinal cutting, making the standard hour-glass handles which are commonly used less effective. Unlike the present invention, the standard handles 22 are too narrow to gain much leverage in rotary cutting motions, and most bothersome is the discomfort experienced after holding them tightly for an hour or so in a tough case. Pushing apically on a standard handle 22 is like squeezing a BB shot between one's fingers, which can be decidedly uncomfortable. The handle 52 (FIGS. 4 and 5) is wide enough to afford easy rotation and is comfortable to hold when applying strong apical forces to shaping files.

FIG. 6A is a schematic view illustrating the potential for the gouging of curved canal walls with a terminal shank-end flute 62. As was called out in FIG. 4, the non-fluted shank 54 of these files is slightly smaller than the terminal shank-end flute, to provide chip space and prevent binding around canal curvatures. This proved to gouge the outside of canal curvatures in prototype testing; therefore it was concluded that some functional design element was needed to support the terminal flute 62 as it traverses severe canal curvatures. FIGS. 6B and 6C, corresponding to FIGS. 4A and 4B, respectively, represent two alternative variations in design which eliminate gouging and maintain smooth continuous canal preparations. FIG. 6B shows a transitional land 66 between the terminal flutes and the smaller shank 54 of the file. FIG. 6C shows a guide ring 68 positioned on the shank 54 of the file at a distance 69 from the terminal flute 62 to support the terminal flutes as they cut around canal curvatures.

FIGS. 7A and 7B show two series of files 50 which are identical in taper for corresponding files in the two figures, except that the extent of the taper of the flutes in the working portion 56 and the lengths of the working portion are different. As is apparent in FIGS. 7A and 7B, the tapers of the flutes in the working portion 56 of the files 50A and 50E shown are less than the tapers shown in files 50D and 50H. In FIG. 7B, the working portion 56 in file 50H is shorter than that in file 50E, thereby limiting the diameter of the largest shank-end cutting flutes, an improvement over the files seen in FIG. 7A without the variable flute lengths.

As may be seen from a comparison of FIGS. 8A and 8B, it has been determined through clinical practice and research that, although different root canal morphologies may require different apical tapers in their final preparation shape, the great majority of canals only need a certain amount of enlargement in the coronal part of the root canal. Creating a single rate of taper through the full length of the root canal is not only unnecessarily difficult, but it needlessly weakens root structure and risks perforation through over-enlargement of curved roots as seen in FIG. 8A.

FIGS. 9A–9C show a non-ISO-tapered file series 90 having the same tapers but different maximal diameters 92, 94, and 96. These variations are useful when treating roots of different widths, files 90A and 90B being appropriate, respectively, for narrow roots and roots of average width (FIG. 10A), and file 90C addressing a wide-rooted tooth (FIG. 10B). Additionally this file set may be used sequentially in the same root, as seen in FIGS. 11A–11C, to serially enlarge the canal.

FIGS. 12A–12D show a variably-tapered Hedstrom file series 100, each with SAFE EDGE™ 102 as disclosed in my prior U.S. Pat. No. 4,836,780, but with the additional safety feature comprising shorter flute lengths 104 as the tapers increase. This is an important modification for the reasons discussed in connection with FIGS. 8A and 8B.

FIGS. 13A–13D show an ISO-tapered file series 110 with flute lengths becoming progressively shorter as the tip diameters become greater.

FIGS. 14A–14D show a set of variably-tapered files 120 which have the same or nearly the same tip diameters with tapers which increase proportionally by 100% from each file to the next. For example, file 120A has a taper of 0.05 (mm/mm); file 120B has a taper of 0.1 mm, file 120C has a taper of 0.2 mm, and file 120D has a taper of 0.4 mm. This allows a short range of tapers to address a large variation in root canal morphologies.

FIGS. 15A–15D show a set of files 130 with a single non-ISO taper with flute lengths becoming progressively shorter as the tip diameters become proportionally greater. In this example, the tips increase 100% from one file to the next, file 130A having a tip diameter of 0.15 mm, file 130B having a tip diameter of 0.3 mm, file 130C having a diameter of 0.6 mm and file 130D having a tip diameter of 1.2 mm. This allows a smaller set of instruments to address a wide range of variation in canal morphology without weakening the root by overshaping.

Figure 15A:
Figure 15B:
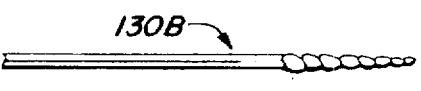
Figure 15C:
Figure 15D:

FIG. 15E shows a single "U" blade file of a set of "U" blade files like that shown in FIGS. 15A–15D, the files all having the same non-ISO taper. The tips vary in diameter by proportional increments as described in the Schilder U.S. Pat. No. 5,017,138.

FIGS. 15F-1 through 15F show a set of negotiation files 140 which are given the designation numbers 07/01, 10/02, 12/03, 15/04 and 17/05. The first number corresponds to tip diameter which increases from 0.075 mm for file 140A to 0.175 mm for file 140B in increments of 0.025 mm. Each of the files has a flute length of 16 mm. The maximum flute diameter increases proportionally from 0.235 mm for file 140A to 0.975 mm for file 140E. Tapers increase in 0.01 mm/mm increments from file 140A with a taper of 0.01 mm/mm to file 140E with a taper of 0.05 mm/mm.

This assortment of increasing tip diameters and tapers with increasing file size allows a 0.15 mm file maximal stiffness which is needed when attempting to find and enter an occluded calcified canal prior to shifting to a 0.075 mm file which provides the maximum tactile response when negotiating the often tortuous terminal aspect of a canal after coronal enlargement with the larger file. The intended procedure with the negotiating files 140 in the set of FIGS. 15F-1 through 15F-5 is to begin with a larger file which is suited to initial penetration and then shift to smaller files which are suited to work into the apical region after the initial opening is cleared.

FIGS. 16A through 16E schematically represent a file 150 which is pre-shaped in accordance with an aspect of my invention. The files 150 are manufactured of a nickel-titanium 11i alloy called Nitinol™. This alloy is a metal with a "memory" which has the capability of retaining a given shape, once established. After the files are fabricated from Nitinol™, the tips are shaped to the preferred degree of curvature in an implement 152 and are held in that shape during an annealing step. This develops the "memory" of the curve near the end or throughout the length of the file. The file 150 is superflexible for the first two-thirds of its length while the hook at the end makes it easier to direct the file down into the apical region of the root canal, particularly where the root is rather tortuously curved or twisted. These files 150 are to be provided in sets according to the variable tapers disclosed herein with respect to ISO-tapered files like that shown in FIG. 1A or sets of non-ISO-tapered files having similar tapers as shown in FIGS. 13, and 15A through 15E and the corresponding descriptions thereof. The sets of files 150 may also have varying degrees of curvature between sets or from one file to the next in a set. Thus, there will be a set of files 150 having a first pre-set curvature, another set of files 150 having a different pre-set curvature and additional sets of pre-shaped files corresponding to any desired curvature or shape.

FIG. 16F shows a file 151 having dulled cutting edges 153 along one side of the file. The file 151 is constructed of Nitinol™ and pre-curved as are the files in views A through E of FIG. 16 but the curve imparted into the memory of the file during the fabrication process extends throughout its fluted portion. This configuration of a SAFE EDGE™ file of my prior patent insures that the non-cutting side of the flutes automatically follows the inner side of the curved root, thereby further protecting against perforation.

Turning now to the series of FIG. 17, FIGS. 17C through 17I schematically represent different types of implements which are to be used with correspondingly shaped files, such as the files 50 in FIGS. 17A and 17B, in systems in accordance with the present invention in the preparation and filling of a root canal. (Note that the flutes of file 50 in FIG. 17B are formed in a counterclockwise direction, opposite to the file in FIG. 17A.) Each of these implements is designed to be provided in a set, corresponding to the sets of files of varying tapers as described hereinabove.

FIG. 17C represents an irrigating cannula 200 comprising a shaft 202 mounted in a head 204. The cannula 200 has a hollow bore 206. The shaft 202 is tapered, beginning at the point 208, and terminating in a fine tip 210. The tapered shape aids in displacement of fluids throughout the length of the canal, providing a more effective way to freshen the irrigation fluids at the end of the canal than irrigation cannulas currently available. Transverse opening 212 communicates with the hollow bore 206 to permit irrigating fluid to be directed into the apical region of the root canal to remove debris developed by using a set of files such as 50 (FIGS. 4 and 5). A set of variable taper cannulas is provided to match the variable taper files such as 50.

View 17D of FIG. 17 represents a paper point 220 which is used to dry a root canal. The paper point 220 is shaped similarly to the files, as described hereinabove, and has a corresponding taper beginning at the point 222 and terminating at a fine tip 224. A set of paper points 220 is provided to match the variable taper files such as 50 (FIGS. 4 and 5).

Commercially available paper points are invariably white. I have discovered, however, certain beneficial results from using colored paper points, preferably in a pastel shade which possesses the property of changing color when moistened. White paper points do not noticeably change color when wet. However, a colored paper point possesses the capability of displaying the length of the root canal in those instances were the root canal is kept patent to its terminus, in which case the paper point can be inserted beyond the terminus to be moistened by jaw tissues apical to the tooth. There is also a telltale indication if the canal is not completely dried. Good results have been obtained with salmon-colored, aqua-colored, beige-colored and green pastel-colored paper points which exhibit a definitely noticeable change of color when moistened. Thus, the paper point 220 may be considered to be colored in one of the shades in the group of green pastel-colored, salmon-colored, aqua-colored and beige-colored in preferred embodiments of the invention. For convenience in selecting corresponding files, the handles of the files may be provided with corresponding colors.

FIG. 17E represents a gutta percha point 230 having a taper corresponding to the files described hereinabove beginning at a point 232 and terminating at a fine point 234. After the paper point 220 is used to dry the interior of the root canal, a gutta percha point such as 230 is pushed into the apical region and packed tightly to fill the apical region of the root canal. It is important to note that the shank end is not tapered, reflecting the maximum flute diameters of corresponding files shown in FIG. 17A.

FIG. 17G represents a gutta percha obturating carrier 240 with gutta percha filling material 246 installed thereon. The carrier 240 tapers in the manner previously described, beginning at the corresponding point 242 and continuing to its termination at the tip 244. Conventional obturating carriers are smoothly tapered from shank to tip. A set of such carriers may be provided to match the shapes described hereinabove for the sets of files 50. However, in a variant of this embodiment, I propose an obturating carrier provided with flutes along its tapered portion, essentially like the flutes 60 on the file 50 in FIG. 17A except for the direction of the spiral. It will be understood that FIG. 17H may be taken to schematically represent such a fluted region between the point 242 and the tip 244. Along this fluted region, the flutes are in a counterclockwise spiral, viewed from the proximal end of the carrier 240'. This obturating carrier has similar shapes as the files in FIGS. 17A and 17B and it may be used alongside a previously fit gutta percha cone, to thermoplastisize the gutta percha, or the carrier may be coated with pre-heating alpha and/or beta phases gutta percha and carried into the canal. By running the carrier handpiece, the carrier backs out of this canal, leaving canals filled with the material.

Finally. FIG. 17I represents a restorative post 250, tapered as described beginning at the point 252 and continuing to its termination 254. The end 254 is not as finely pointed as is shown for the cannula 200, paper point 220 and gutta percha point 230 because its tapered length is shorter than those other implements. The restorative post 250 is designed to be anchored in the root canal at a position short of the terminal end of the canal.

FIG. 18A is a schematic view of a heat carrier/plugger tool 260 modified in accordance with my invention. This tool is shown installed in a handpiece 262 (in broken outline) having a chuck 264 (also in broken outline) for tightening the tool 260 in the handpiece 262.

The heat carrier/plugger 260 has a gooseneck bend near the point A leading to a straight section terminating in an extended tapered tip 266. A condensing portion 265 is made of stainless steel with a hollow core through which a conductor (not shown) extends for providing connection to an electrical circuit. When the circuit is energized, the stainless steel heater 265, being of relatively high resistance material, develops heat at the very end for softening the gutta percha material with which it is used.

When used in the practice of my method in filling a root canal with gutta percha material in a single compression wave, existing heat carrier/pluggers have a tendency to bend in the mid portion. I provide a thin stainless steel support member 268 which is welded or soldered to the tool 260 along the back thereof between the points A and B, along line 270. The shape of the support member 268 in the region between points B and C conforms closely to the shape of the nose of the chuck 264 of the handpiece 262 but is not affixed thereto. This permits the chuck 264 to be rotated during tightening and loosening of the shank of the tool 260 while limiting the extent that the tool can give during use, since the slightest bend brings the adjacent surface of the support member 268C into contact with the nose of the chuck 264 and prevents any further bending.

FIG. 18B shows two versions of the heat carrier/plugger tool 260 of FIG. 18A associated with respectively corresponding gutta percha cones. In the pair designated A, the gutta percha cone has the traditional taper of presently used gutta percha cones. The heat carrier/plugger 260A is provided with a taper which corresponds to these traditional tapers, thereby enabling the tool to be inserted into or near the apical region of the root in a single wave of condensation. In the pair designated B in FIG. 18B, the gutta percha point is like the point 230 in view E of FIG. 17 with a taper beginning at point 232 and extending to the fine tip 234. The tapered portion 266 of the heat carrier/plugger 260B begins at a point 267 and corresponds to the tapered portion of the gutta percha point 230. Use of the heat carrier/plugger 260 in the canal filling method of my invention is represented schematically in FIG. 19.

In FIG. 19, the heat carrier/plugger 260 is tapered to correspond to the shape of the canal which has been formed prior to the filling step. The taper may correspond to that of tool 260A for use with conventional tapered gutta percha cones prepared by using other shaping files or it may have the taper of the terminal portion 266 of the tool 260B, corresponding to the taper in the terminal portion of the gutta percha point 230 (see FIG. 18B). As indicated in FIG. 19, view A, the gutta percha point is fully inserted into the root canal. The distal end of the heat carrier/plugger 260 is inserted into the canal cervical region and energized to soften and permit the heated tip element 265 to move through the gutta percha material within the canal. As the tool 260 moves further into the root canal, it develops hydraulic pressure which forces the softened gutta percha material and sealer cement into the lateral branch portions of the canal, represented at 274. Finally, as shown in view C, the heat carrier/plugger 260 is withdrawn, leaving the lateral branches 274 and the apical portion of the root canal filled and sealed with the obturation materials.

FIG. 20 (views A through D) shows a tapered heat carrier/plugging tool 300 as it is used to soften and downpack through a pre-fit gutta percha cone 246 in a continuous wave of condensation. FIG. 20A shows the electric heat carrier/plugger 302 withdrawn into its condensation sheath 304 in preparation for heating and compacting gutta percha into the canal. FIG. 20B shows the first move into the canal with the heat carrier on high heat level, with the tool searing into the gutta percha cone until the compaction sheath binds the canal near its orifice level, thus creating the secondary seal necessary for a closed system within which to exert optimally controlled hydraulic compaction forces on the heat-softened gutta percha and the less viscous sealer against the canal walls. FIG. 20C shows the second move into the canal as the heat carrier/plugger 302 is extended out of the compaction sheath 304, heating and plastically deforming the gutta percha and sealer into all dimensions of the root canal system. FIG. 20D shows the withdrawal of the tool 300 from the canal after the extended heat carrier/plugger 302 bottoms out near the apical terminus of the canal, with the soft sticky surplus gutta percha and sealer removed from the canal on the tool. The canal is shown ready for restorative post placement of the type specified in FIG. 17, or for backfilling with the tool and material shown in FIG. 21.

FIG. 21 shows another electric heat carrier of a configuration to afford fast ideal backfilling of canals which have been downpacked but not posted. FIG. 21A shows a preformed gutta percha plug 230 with the shape of the empty coronal part of the canal and a groove or hole 231 to allow introduction of the narrow electric heat carrier of FIG. 21B. FIG. 21B shows a tool 320 whereby a narrow, parallel heat carrier 322 extends through the end of a hollow or notched plugger 324. FIG. 21C shows a gutta percha plug 230 mounted on the backfilling tool 320, and that set of tool and materials placed in the empty coronal part of the canal with sealer 326. FIG. 21D shows that same tool/material set after heat has been created by the heat carrier 322, softening the end of the gutta percha plug 230. As the heat carrier tip 322 is withdrawn coronally, the plugger 324 is pushed apically, thereby condensing the gutta percha 230 from its tip to its butt end. FIG. 21E shows the termination of backfilling as the heat carrier tip 322 is fully retracted into the plugger 324, resulting in a dense obturation of the softened gutta percha.

Although there have been described hereinabove various specific arrangements of an endodontic treatment system in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. An implement for use in obturating a previously prepared root canal having been formed in at least its apical portion by a file having a preselected taper and said root canal having a tapered gutta percha cone which itself has a taper corresponding to the taper of the file used to form said apical portion, said gutta percha cone having been sealed in the root canal in the vicinity of said apical portion; said implement comprising a heat carrier/plugger adapted for securing in a handpiece by means of an adjustable chuck on the handpiece; said heat carrier/plugger having a shank portion for installation in a handpiece, a curved portion extending from said shank portion to an elongated tip portion, said tip portion having a preselected taper corresponding to the taper of the file used to form the apical portion of the canal, and stiffening means affixed to a portion of said curved portion adjacent the shank portion to limit the bending of the heat carrier/plugger due to apically directed force applied thereto from the handpiece during use of said implement.

2. The device of claim 1 wherein said stiffening means comprises a thin stainless steel support member affixed to the heat carrier/plugger adjacent the shank portion.

3. The device of claim 2 wherein said support member is affixed to the heat carrier/plugger by silver solder.

4. The device of claim 2 wherein the support member has an edge which is shaped to match the curved portion of the heat carrier/plugger along the back thereof and is welded to the back of the heat carrier/plugger along said edge.

5. The device of claim 4 wherein the support member has a further edge portion extending along the shank portion but spaced therefrom which is shaped to match the shape of the forward end of the handpiece in order to gain support from the handpiece when in use while providing clearance to permit adjustment of said chuck.

6. The device of claim 2 wherein the preselected taper of the forward portion of the heat carrier/plugger is selected to conform to a traditional taper of ISO-standard gutta percha cones.

7. The device of claim 2 wherein the preselected taper terminates a predetermined distance back from the tip.

8. The device of claim 2 wherein at least the tip portion of said heat carrier/plugger is fabricated of relatively high resistance material for developing heat at the end of the tip portion when the heat carrier/plugger is energized by an electrical circuit.

9. The device of claim 8 wherein said material is stainless steel.

10. The device of claim 9 wherein said heat carrier/plugger has a hollow core for receiving an electrical conductor.

11. The device of claim 1 wherein said tip portion terminates in a tip having a diameter which is greater than the tip diameter of the file used in forming the root canal.

12. The device of claim 11 wherein said tip diameter is effective to bind the heat carrier/plugger in the canal short of the canal terminus.

13. The device of claim 12 wherein said tip diameter is such as to bind the heat carrier/plugger in the canal at a distance between three and five mm short of the canal terminus.

* * * * *